(12) United States Patent
Wang

(10) Patent No.: US 10,582,996 B2
(45) Date of Patent: Mar. 10, 2020

(54) BIODEGRADABLE VASCULAR GRAFTS

(71) Applicant: UNIVERSITY OF PITTSBURGH—OF THE COMMONWEALTH SYSTEM OF HIGHER EDUCATION, Pittsburgh, PA (US)

(72) Inventor: Yadong Wang, Allison Park, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 899 days.

(21) Appl. No.: 14/365,987

(22) PCT Filed: Dec. 21, 2012

(86) PCT No.: PCT/US2012/071389
§ 371 (c)(1),
(2) Date: Jun. 16, 2014

(87) PCT Pub. No.: WO2013/154612
PCT Pub. Date: Oct. 17, 2013

(65) Prior Publication Data
US 2014/0309726 A1 Oct. 16, 2014

Related U.S. Application Data

(60) Provisional application No. 61/579,585, filed on Dec. 22, 2011.

(51) Int. Cl.
*A61F 2/06* (2013.01)
*A61L 27/18* (2006.01)
(Continued)

(52) U.S. Cl.
CPC ........... *A61F 2/06* (2013.01); *A61L 27/18* (2013.01); *A61L 27/20* (2013.01); *A61L 27/507* (2013.01);
(Continued)

(58) Field of Classification Search
CPC .................. C12N 11/08; A61F 2/06
See application file for complete search history.

(56) References Cited

U.S. PATENT DOCUMENTS

2005/0233062 A1* 10/2005 Hossainy ............... A61F 2/82
427/2.1
2006/0020328 A1 1/2006 Tan
(Continued)

OTHER PUBLICATIONS

Jason A. Burdick; Robert L. Mauck, Biomaterials for Tissue Engineering Applications, Dec. 7, 2010, Springer Science & Business Media, 1st Edition, p. 100.*
(Continued)

*Primary Examiner* — Yashita Sharma
(74) *Attorney, Agent, or Firm* — Klarquist Sparkman, LLP

(57) ABSTRACT

Disclosed herein are biodegradable scaffolds for in situ tissue engineering. In some examples, biodegradable vascular grafts and methods of fabricating and uses of such are disclosed. In some examples, a vascular graft includes a biodegradable scaffold including a biodegradable polyester tubular core, a biodegradable polyester electrospun outer sheath surrounding the biodegradable polyester tubular core and/or a thromboresistant agent, such as heparin, coating the biodegradable scaffold. The disclosed vascular grafts can be used for forming a blood vessel of less than 6 mm, including, but not limited to a coronary or peripheral arterial.

15 Claims, 12 Drawing Sheets

(51) Int. Cl.
    *A61L 27/50*     (2006.01)
    *A61L 27/54*     (2006.01)
    *A61L 27/56*     (2006.01)
    *A61L 27/20*     (2006.01)

(52) U.S. Cl.
    CPC ............... *A61L 27/54* (2013.01); *A61L 27/56* (2013.01); *A61F 2210/0004* (2013.01); *A61L 2300/42* (2013.01)

(56) References Cited

U.S. PATENT DOCUMENTS

| | | | |
|---|---|---|---|
| 2006/0085063 A1* | 4/2006 | Shastri | A61F 2/02 623/1.41 |
| 2007/0128171 A1* | 6/2007 | Tranquillo | A61L 27/3808 424/93.7 |
| 2008/0112998 A1* | 5/2008 | Wang | A61K 35/32 424/423 |
| 2008/0260798 A1 | 10/2008 | Freyman et al. | |
| 2009/0011486 A1* | 1/2009 | Bettinger | C08G 63/20 435/180 |

OTHER PUBLICATIONS

Amoabediny et al., "The role of biodegradable engineered scaffold in tissue engineering," *Biomaterials Science and Engineering*, pp. 153-172, Sep. 15, 2011.

International Search Report and Written Opinion, dated Nov. 19, 2013, by the Korean Intellectual Property Office, for PCT Application No. PCT/US2012/071389, 15 pp.

Lee et al., "Substantial expression of mature elastin in arterial constructs," *PNAS*, vol. 108, No. 7, pp. 2705-2710, Feb. 15, 2011.

Wang et al., "A tough biodegradable elastomer," *Nature Biotechnology*, vol. 20, pp. 602-606, Jun. 2002.

Allen, et al. "Nerve regeneration and elastin formation within poly (glycerol sebacate)-based synthetic arterial grafts one-year post-implantation in a rat model." *Biomaterials* 35, No. 1 (2014): 165-173.

Crapo, et al. "Physiologic compliance in engineered small-diameter arterial constructs based on an elastomeric substrate." *Biomaterials* 31, No. 7 (2010): 1626-1635.

Hong, et al. "A small diameter, fibrous vascular conduit generated from a poly (ester urethane) urea and phospholipid polymer blend." *Biomaterials* 30, No. 13 (2009): 2457-2467.

Soletti, et al. "In vivo performance of a phospholipid-coated bioerodable elastomeric graft for small-diameter vascular applications." *Journal of Biomaterials Research Part A* 96, No. 2 (2011): 436-448.

Lee et al., "A biodegradable synthetic graft for small arteries matches the performance of autologous vein in rat carotid arteries." *Biomaterials* 181, (2018): 67-80.

\* cited by examiner

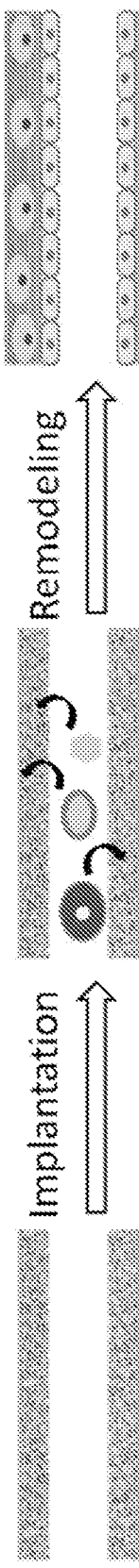
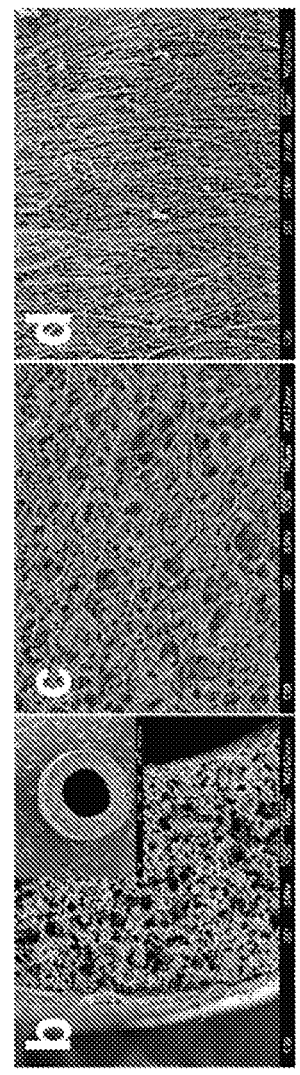
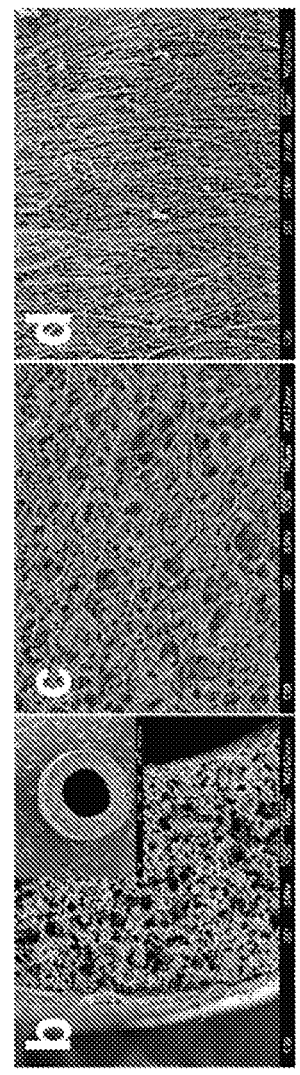
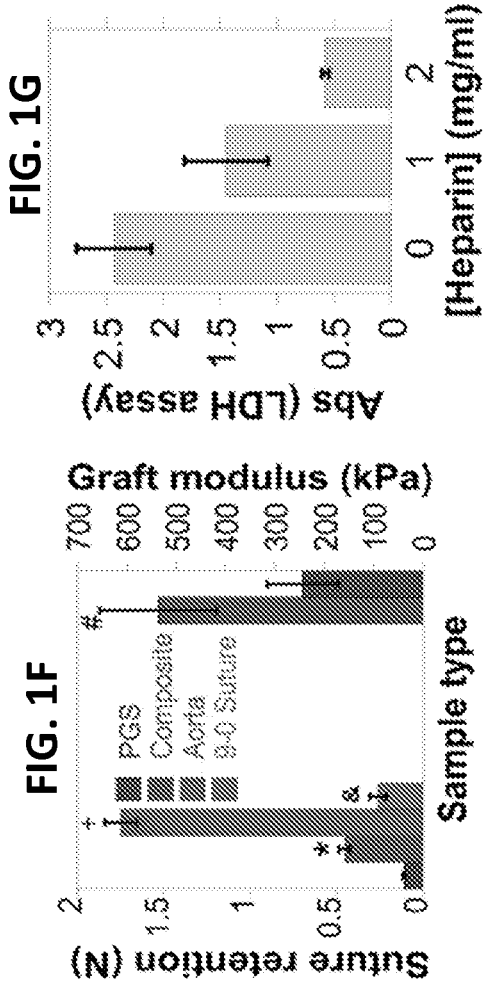
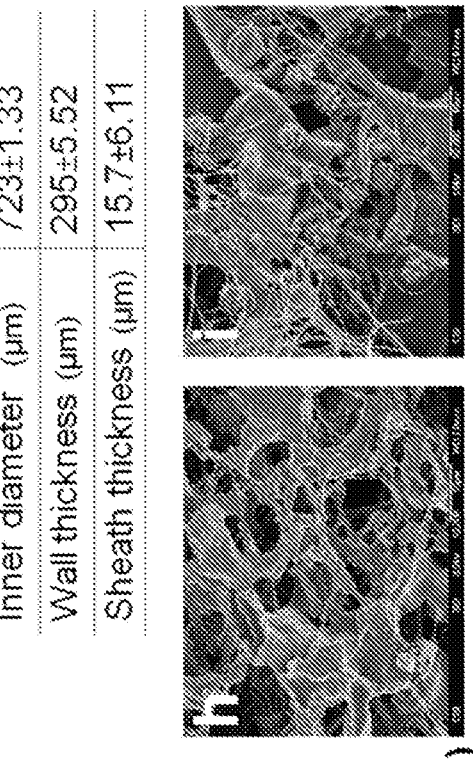

FIG. 3A
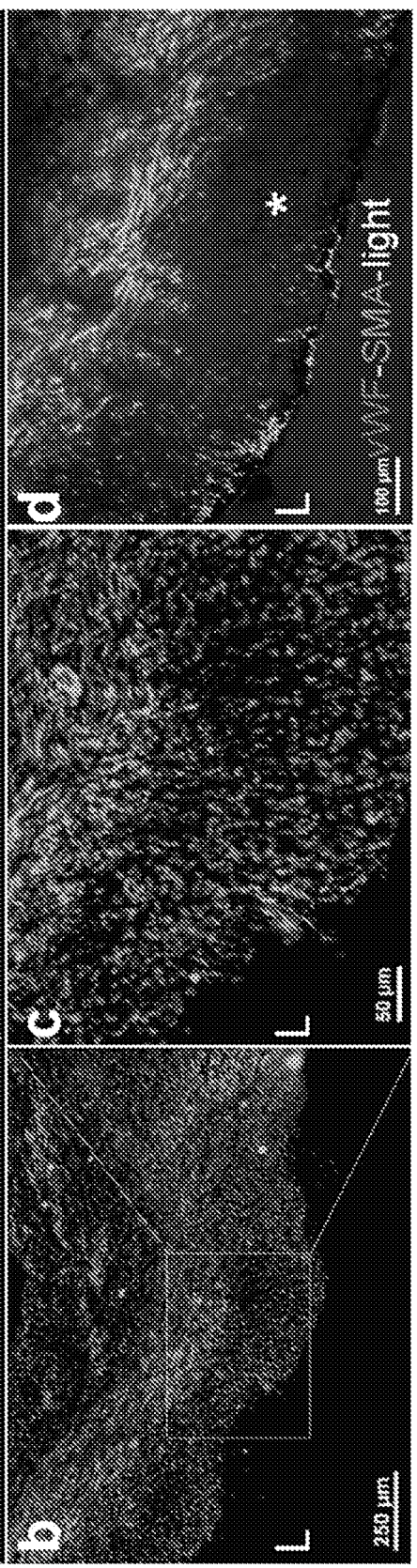
FIG. 3B
FIG. 3C
FIG. 3D

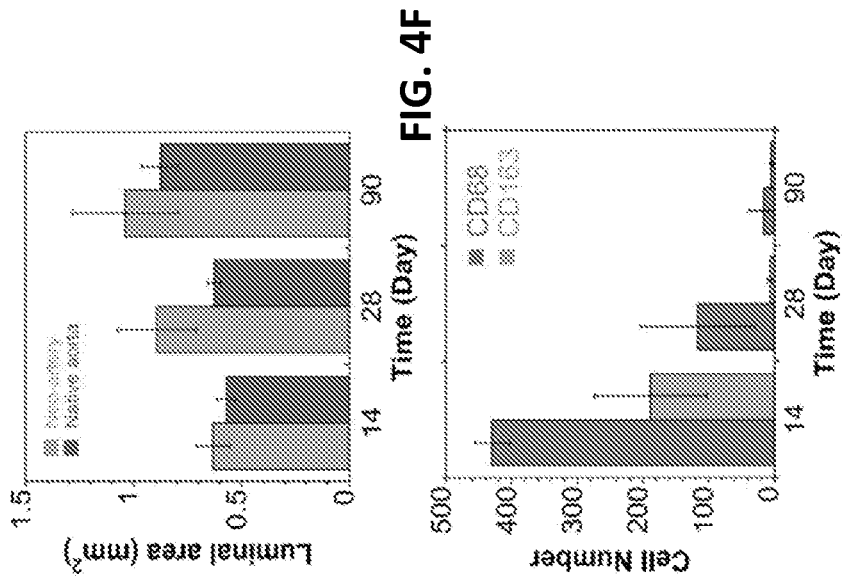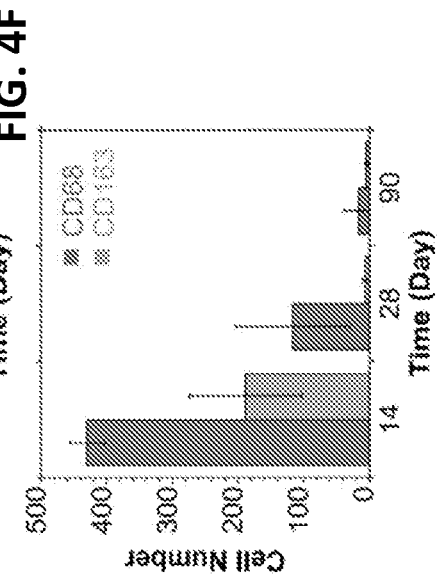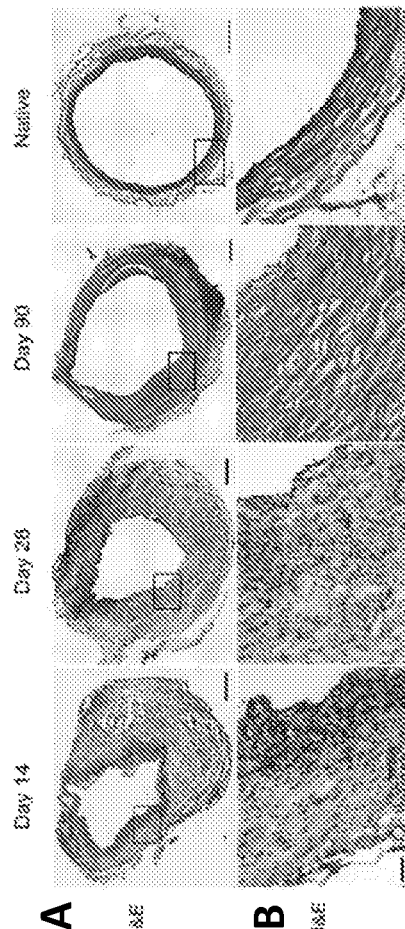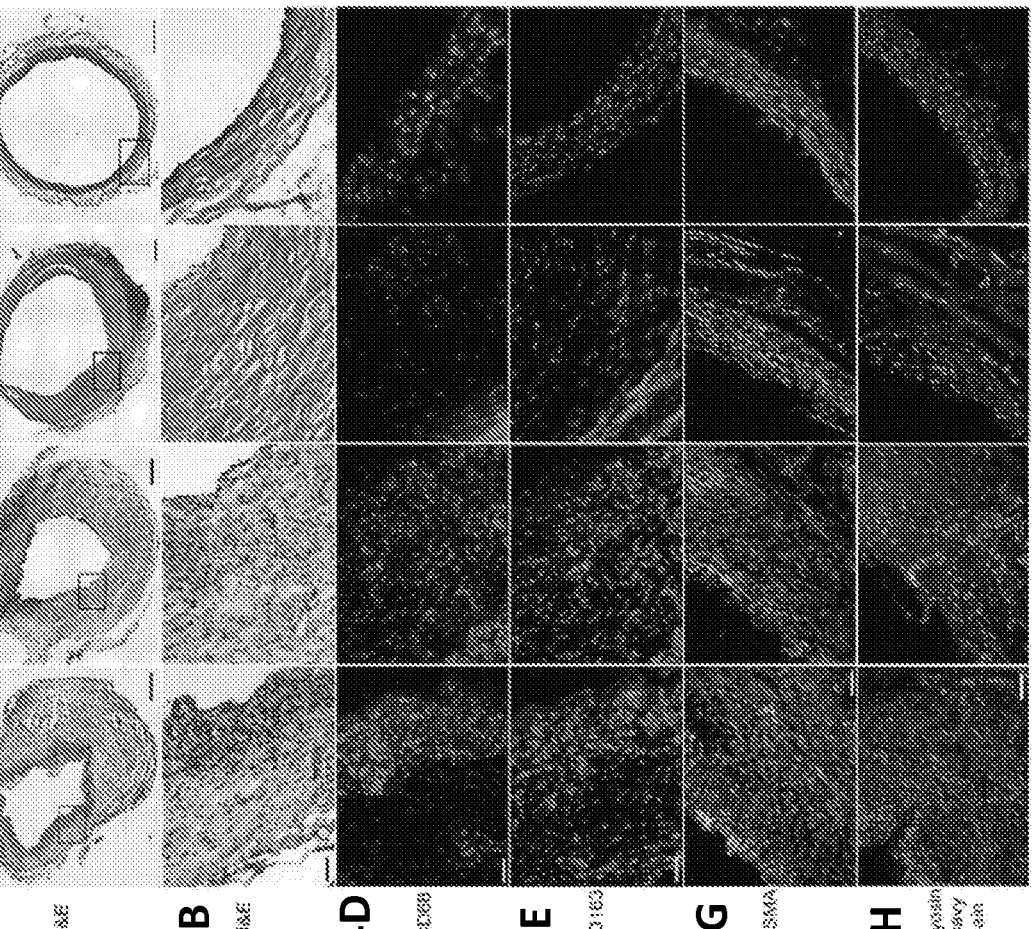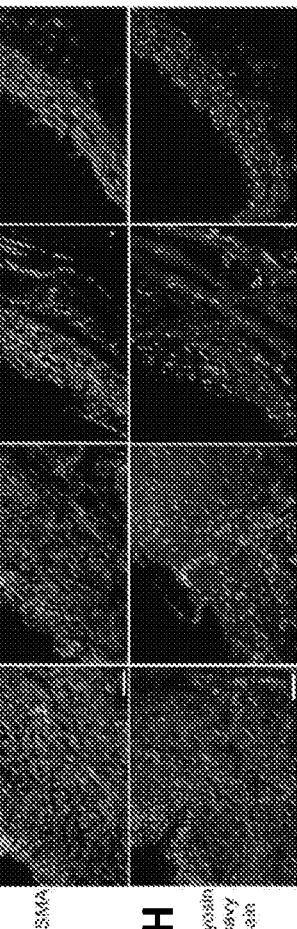

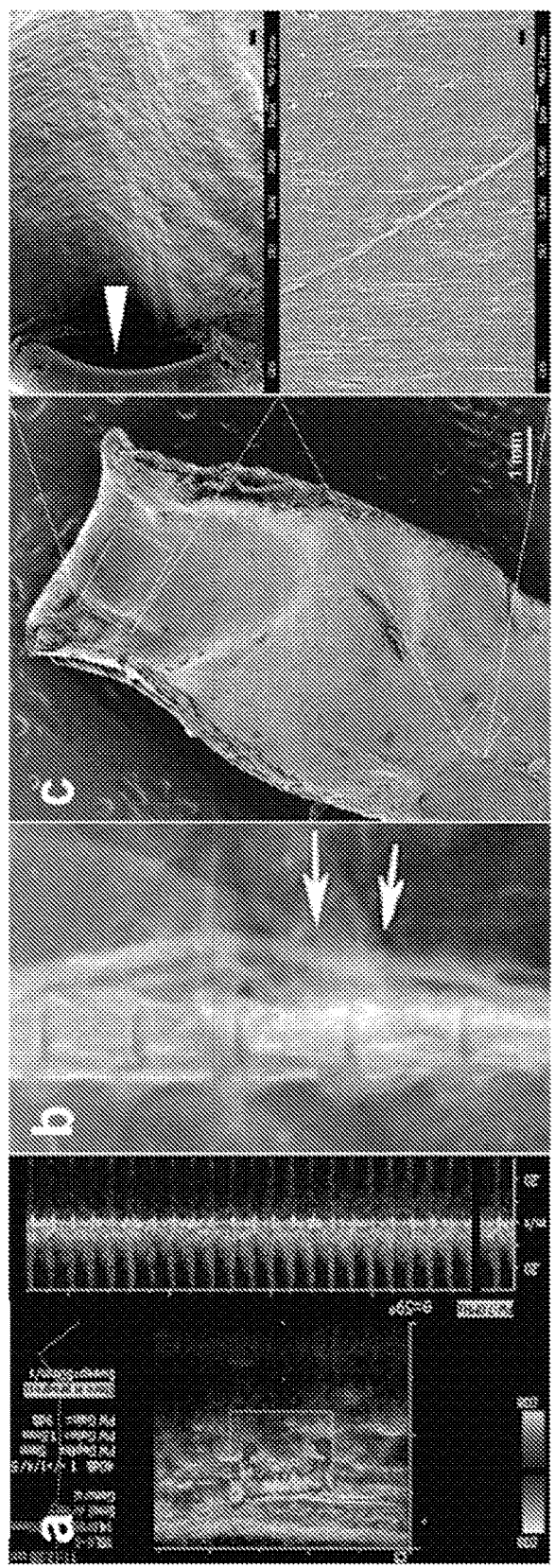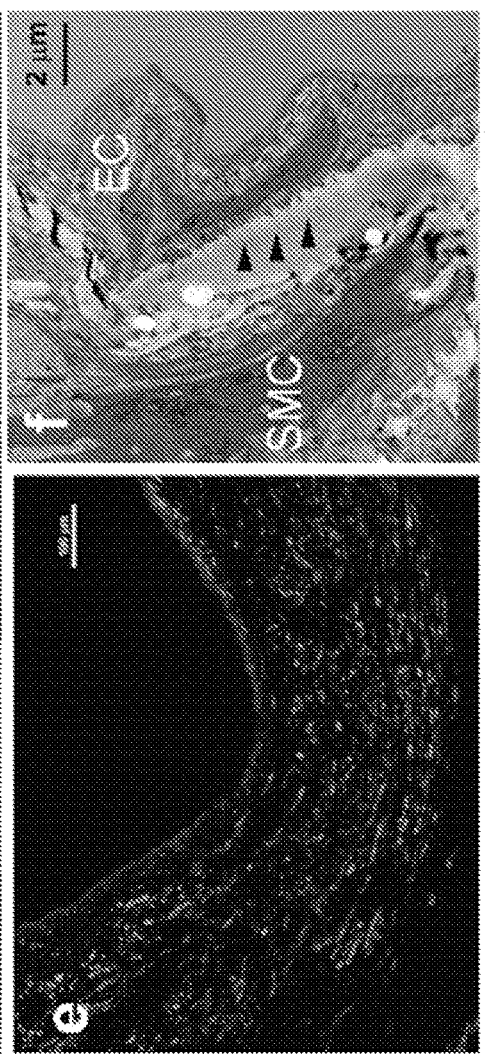

FIG. 7A
FIG. 7B
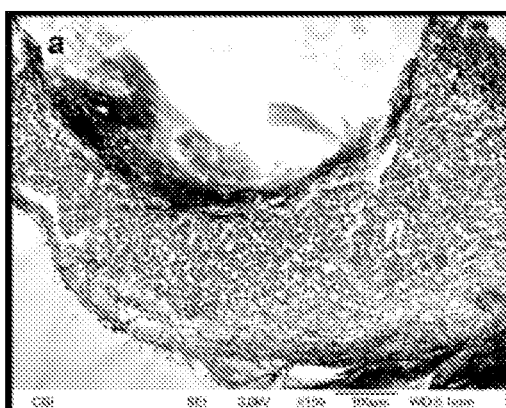
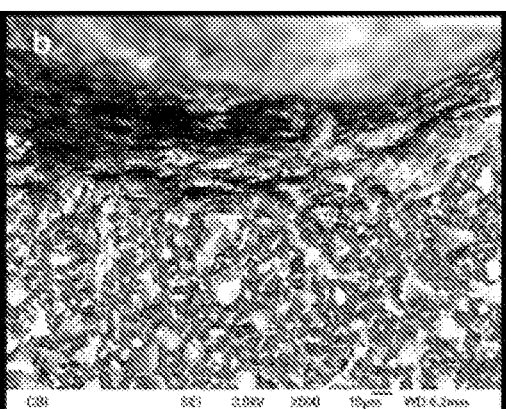
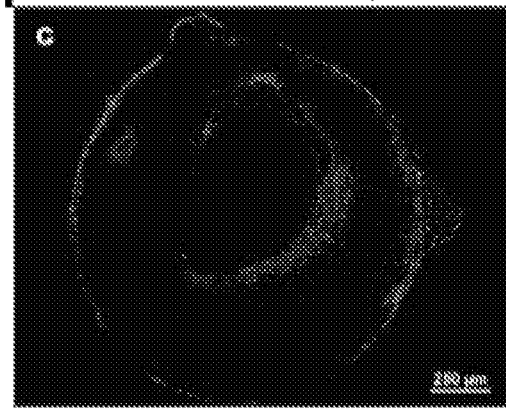
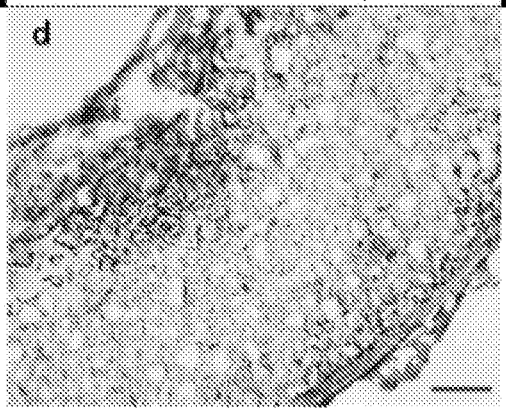
FIG. 7C
FIG. 7D

FIG. 10A  FIG. 10B
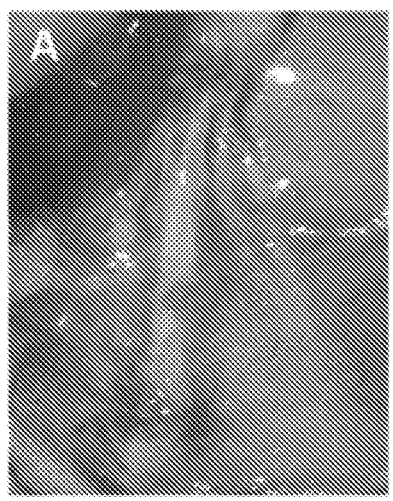
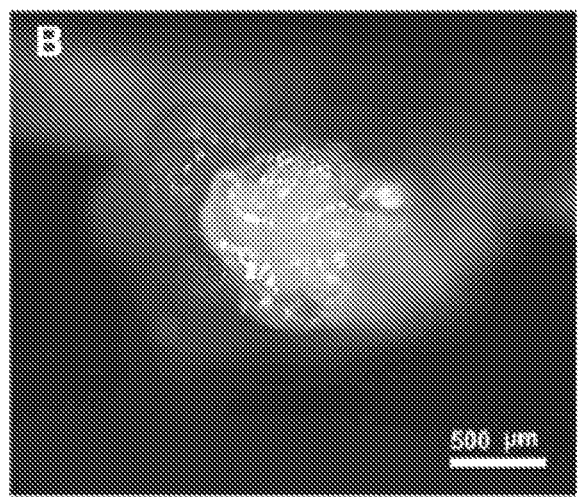
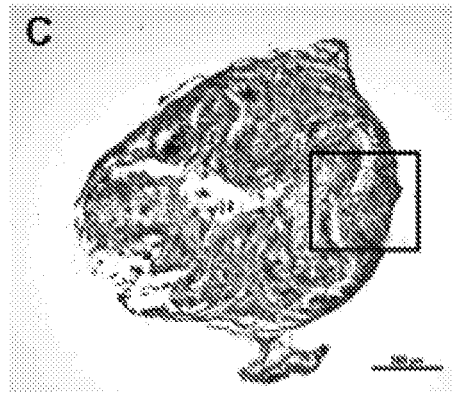
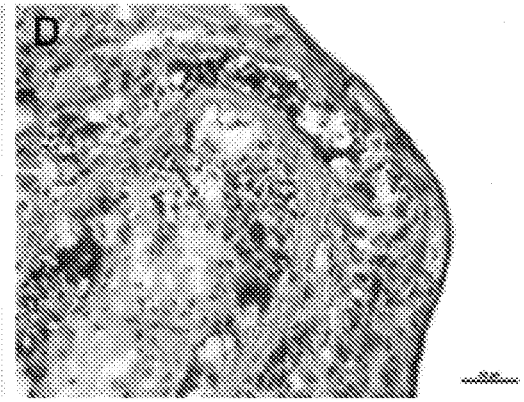
FIG. 10C  FIG. 10D

FIG. 11A
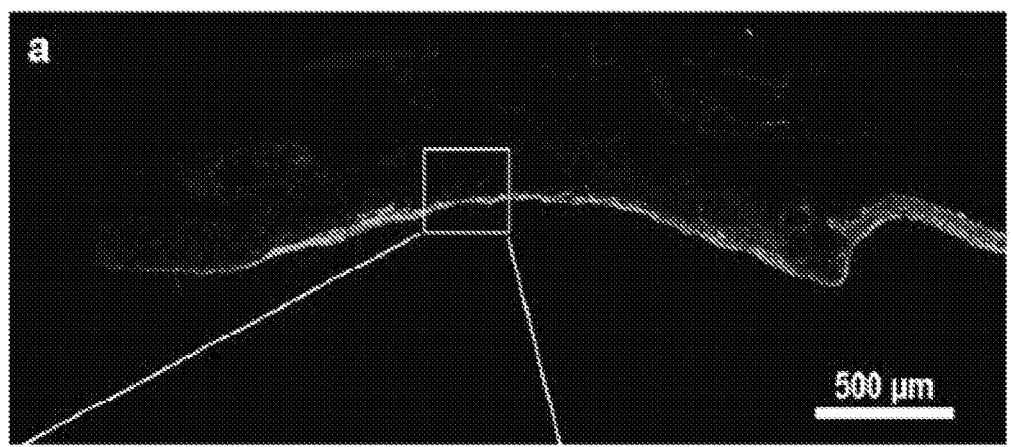
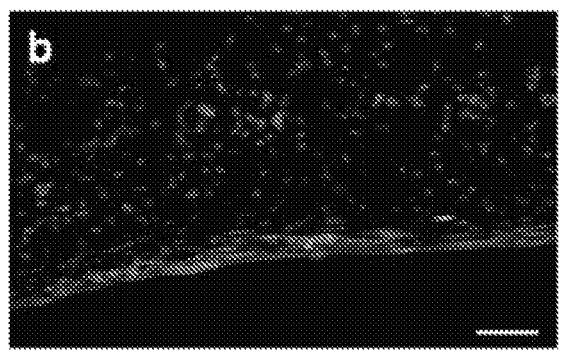
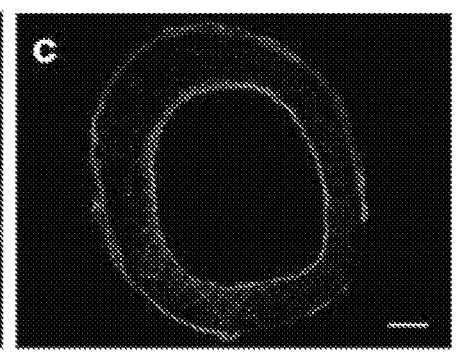
FIG. 11B  FIG. 11C

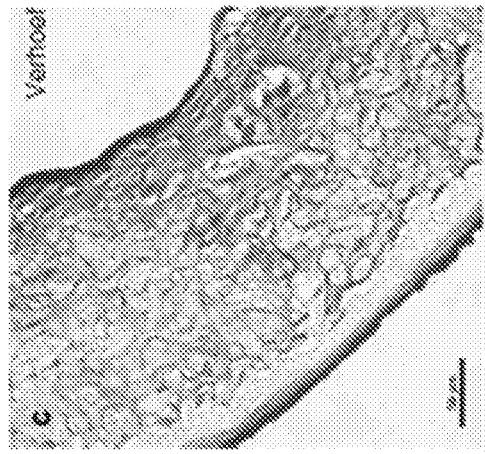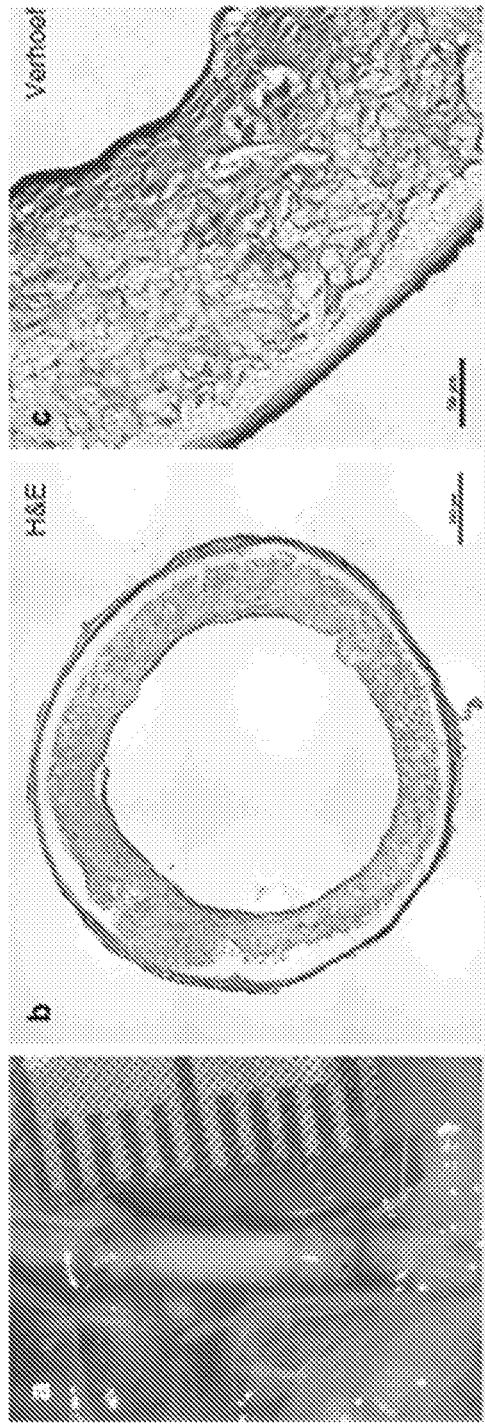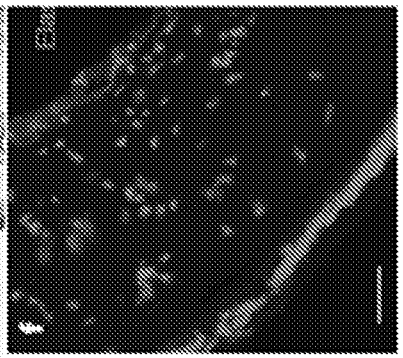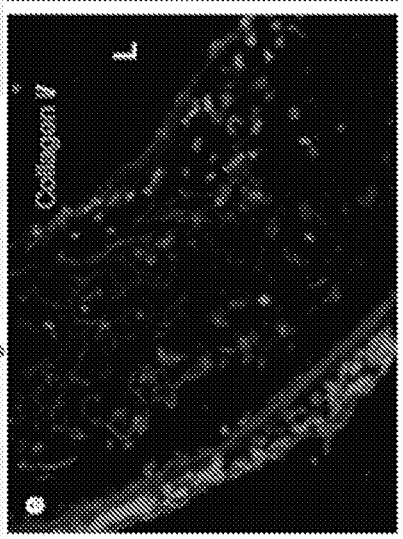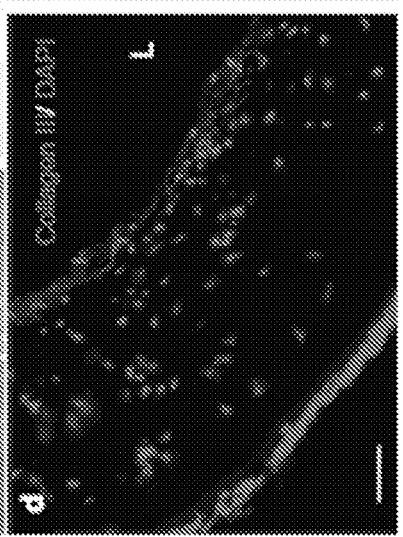
FIG. 12A  FIG. 12B  FIG. 12C
FIG. 12D  FIG. 12E  FIG. 12F

BIODEGRADABLE VASCULAR GRAFTS

CROSS REFERENCE TO RELATED APPLICATIONS

This is the U.S. National Stage of International Application No. PCT/US2012/071389, filed Dec. 21, 2012, which was published in English under PCT Article 21(2), which in turn claims the benefit of U.S. Provisional Application No. 61/579,585, filed Dec. 22, 2011, which is incorporated herein in its entirety.

ACKNOWLEDGMENT OF GOVERNMENT SUPPORT

This invention was made with government support under grant number HL089658 awarded by National Institutes of Health. The government has certain rights in the invention.

FIELD

This disclosure relates to biomaterials that promote tissue and organ regeneration and specifically to those that are biodegradable, such as biodegradable vascular grafts including a heparin-coated poly(glycerol sebacate)(PGS) scaffold with a poly(caprolactone) (PCL) sheath and methods of making and use thereof.

BACKGROUND

Small-diameter arterial substitutes are urgently needed as incidences of atherosclerotic arterial disease, especially coronary artery disease, rises with an aging population and increasing obesity. Autologous vessels are commonly used for bypass surgery to replace diseased and damaged arteries with an inner diameter less than 6 mm. However, autografts have several limitations including low availability, donor site morbidity, compliance mismatch, and late intimal hyperplasia, which often cause graft failure. Tissue engineering is an alternative to autografts with the potential to develop small-diameter arterial constructs that are nonthrombogenic, strong, and compliant. Yet, neither synthetic nor tissue-engineered grafts have yet to show clinical effectiveness in arteries smaller than 6 mm. Therefore, a need exists for small-diameter arterial substitutes that are nonthrombogenic, strong and compliant, but are effective in arteries less than 6 mm.

SUMMARY

Host remodeling is important for the success of medical implants including vascular substitutes. A conceptual breakthrough in this disclosure is that properly designed scaffold made from rationally designed biomaterials can induce host tissue remodeling into a regeneration process. This bypasses the cell seeding and cell culture steps that are time consuming and costly, but are associated with typical tissue engineering strategies. This breakthrough is pivotal for translation of tissue engineering into practical utility in patient care. This concept is universally useful in many organs; the specific utility disclosed here is blood vessel, specifically artery.

Because artery is an elastic tissue an elastomer is used as a scaffold material. Chronic inflammation in response to the presence of foreign materials leads to fibrous encapsulation and scar tissue formation, thus to avoid scar and to regeneration artery, the specific materials of choice here were selected to degrade quickly. Furthermore, in some embodiments, to encourage host cell migration into the scaffold, a porous scaffold is used. It should be noted that this concept of matching mechanical property, proper porosity and appropriate degradation is applicable to other material and other tissues. This can serve as a guiding principle for inductive, in situ tissue engineering in vivo (i.e., tissue engineering without cell seeding prior to implantation).

Synthetic and tissue-engineered grafts have yet to show clinical effectiveness in arteries smaller than 6 mm. The inventors disclose herein cell-free biodegradable elastomeric grafts that degrade rapidly to yield neo-arteries nearly free of foreign materials 3 months after interposition grafting. This design focuses on enabling rapid host remodeling. Three months post-implantation, the neo-arteries resemble native arteries in the following aspects: regular, strong and synchronous pulsation, a confluent endothelium and contractile smooth muscle layers, co-expression of elastin, collagen and glycosaminoglycan, and tough and compliant mechanical properties. This cell-free approach represents a philosophical shift from the prevailing focus on cells in vascular tissue engineering, and may impact regenerative medicine in general.

As such, disclosed herein are biodegradable scaffolds, such as tissue engineering scaffolds, which can be used for the replacement and/or repair of damaged native tissues. In some embodiments, the disclosed scaffolds are included within a vascular graft. In some embodiments, a vascular graft includes a biodegradable scaffold comprising a biodegradable polymer tubular core. The biodegradable scaffold can further comprise a biodegradable polymer electrospun outer sheath surrounding the biodegradable polymer tubular core and/or a thromboresistant agent, such as heparin, coating the biodegradable scaffold. The disclosed vascular grafts can be used for forming a blood vessel of less than 6 mm, including, but not limited to a coronary or peripheral arterial.

Also disclosed are methods of fabricating a biodegradable scaffold and in particular a biodegradable vascular graft. In some embodiments, the method of fabricating a biodegradable vascular graft includes preparing a biodegradable poly(glycerol sebacate) (PGS) tubular core; surrounding the biodegradable polyester tubular core with a poly(caprolactone) (PCL) sheath; and coating an inner luminal surface of the biodegradable PGS tubular core with a thromboresistant agent, thereby forming a biodegradable vascular graft, in which at least 75% of the vascular graft degrades within 90 days of implantation in a subject.

The foregoing and other features and advantages of the disclosure will become more apparent from the following detailed description, which proceeds with reference to the accompanying figures.

BRIEF DESCRIPTION OF THE DRAWINGS

FIG. 1 shows the characterization of the composite graft and the overall scheme of its application. (a) Schematic representation of direct implantation of the cell-free graft and the proposed remodeling process of the graft into a biological neo-artery. (b) SEM images of the bi-layered structure of the PGS tubular core with PCL electrospun sheath, scale bar, 100 µm. Inset: top view of the graft. (c) Lumen of the PGS tube, scale bar, 100 µm. (d) The PCL fibrous sheath, scale bar, 10 µm. (e) Graft parameters as identified by micro-CT examination. (f) Suture retention test demonstrates that the sheath effectively improves the pull out strength of the graft. Suture pull out strength of the composite graft is higher than the break force (&) of 9-0 suture (n=5). p<0.05: + composite graft vs. 9-0 suture, + composite graft vs. rat aorta, # composite graft modulus (n=8) vs. that of the PGS tube (n=3). (g) Adsorption of heparin on PGS effectively reduces platelet adhesion as examined by lactate dehydrogenase assay (P<0.0001 between all groups). (h) Heparin adsorbs well on PGS surface to reduce fibrin formation. The few adhered platelets show quiescent morphology, scale bar, 10 µm. (i). Without heparin adsorption, significant amount of fibrin forms on PGS surfaces and the large number of adhered platelets exhibited activated morphology (circle), scale bar, 10 µm. Data represent mean±standard deviation for e-g.

Figure 2A:
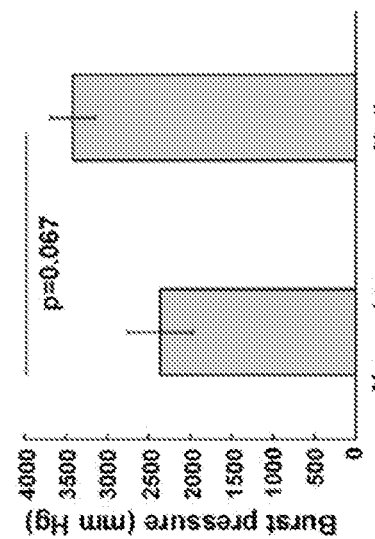

FIG. 2 illustrates remodeling of the synthetic graft. (a) Gross appearance of the graft changed significantly upon host remodeling. Grafts redden, become translucent, and integrate well with host tissue over time. At 90 days, the grafted segment was covered by an adventitia-like tissue and completely integrated with the host tissue. Immunofluorescent staining of adventitial fibroblasts is available in FIG. 11. Non-degradable sutures (black) marked the graft locations. (b) The burst pressure of the neo-artery (n=3) is statistically the same as native aorta (n=4). (c) Stress-strain curve of the neo-artery (day 90) resembles that of the native aorta and is much different from un-implanted grafts. (n=3). Bars represent standard error. (d) Compliance of the neo-artery at 90 days approaches that of native aorta (n=4). Standard errors for unimplanted grafts and PGS core are very small and barely visible at the plotted scale, n=3). Data represent mean±standard error for b-d.

FIG. 3 illustrates extensive smooth muscle cell infiltration occurs within 14 days. (a) Immuofluorescent staining of α-SMA demonstrated extensive smooth muscle cell presence within the remodeled graft wall. The tissue was split longitudinally, half of which is shown. Native aorta is on the right, its border with the graft is indicated by the dashed line, scale bar, 500 µm. L=lumen. (b) Magnified view of the mid-graft shows the presence of a mixed cell population with many α-SMA-negative cells. Nuclei counterstained by DAPI, scale bar, 250 µm. (c) Further magnification of the mid-graft indicates a complicated smooth muscle cell distribution, again suggesting an extensive but complicated remodeling process. Scale bar, 50 µm. (d) Co-staining of vWF and α-SMA merged with the bright-field image (darkened so as not to overwhelm the fluorescent images) indicates the smooth muscle layer is covered by an endothelialized lumen. Dark spots (*) in the bright-field image might be graft material. Scale bar, 100 µm. bright field images of original brightness are in FIG. 8.

FIG. 4 illustrates remodeling of the grafts. (a) H&E staining of the grafts indicate a transition into a neo-artery approaching the native aorta in structure with an apparent adventitia-like tissue. Immunofluorescent staining of adventitial fibroblasts is available in FIG. 11. The vessel wall contains a very small amount of inflammatory cells by 90 days (*). The top of the 14-day sample was trimmed to remove the adjoining vein. Image merged from a panel of 100× micrographs, scale bar, 250 µm. (b) Magnified view to show the remodeling progress within the vessel wall. A substantial amount of ECM stains the vessel wall pink at 14 days. The ECM fibers are aligned circumferentially and the smooth muscle nuclei were elongated and aligned. 200×, scale bar, 50 µm. (c) Luminal area gradually increases with time and there is no statistical difference between the remodeled grafts and the native aorta, suggesting absence of aneurysm and stenosis. (d) CD68 staining of newly recruited macrophages shows the inflammatory response decreases over time and is largely resolved by 90 days. (e) The presence of CD163+ macrophages supports the constructive role of M2 macrophages during the remodeling of the grafts. (f) Total macrophage numbers decrease over time as with CD163+ macrophages, suggesting the remodeling process slows over time. (g) Smooth muscle cells stained with α-SMA are more organized as the grafts are remodeled over time. (h) Strong myosin heavy chain staining indicated contractile phenotype of the smooth muscle cells. All the immunofluorescent micrographs were 200×, with nuclei counterstained by DAPI, scale bar, 50 µm. Data represent mean±standard deviation for c and f.

FIG. 5 includes histological images of the neo-artery revealed the presence and organization of major ECM components at 90 days. (a) The circumferential orientation of the ECM components in the neo-artery resembles that in native aorta. The neo-arteries have thicker vessel walls and contain more cells, suggesting the remodeling process is active, but the neo-artery bears no resemblance of a synthetic graft. Top: day 90 explant, bottom: native aorta. Verhoeff's, Masson's trichrome, and safranin-O staining revealed substantial amounts of elastin (black), collagen, and glycosaminoglycansin in the neo-artery. Elastin antibody stained elastic fibers that distributed thoughout the neo-artery. Type I collagen was less dense in the neo-artery. However, its distribution is consistent with native aorta in that denser collagen I fibers populated the outer (adventitia) side of the vessel. Immunofluorescent staining of collagen III showed a wide distribution throughout the artery, as in native aorta. (b) Quantification of elastin (n=4) and total collagen (n=4) showed that neo-arteries contain 77% the elastin of the native aortas and the same amount of collagen. Data represent mean±standard deviation.

FIG. 6 shows endothelialization of the neo-artery and vascular patency as examined at day 90. (a) Laser Doppler ultrasound imaging indicates excellent patency and regular synchronous pulsation with host aorta. (b) Angiography confirms the ultrasound examination and shows a patent lumen. Arrows indicate the graft location. (c) SEM of day 90 explant shows a smooth transition from host to neo-artery with a consistent diameter. Vessel split longitudinally, scale bar, 1 mm. Higher magnification micrographs show the endothelializaiton at the anastomosis (suture indicated by the arrowhead, scale bar, 10 µm) and mid-graft (scale bar, 1 lam). (d) vWF staining (red) demonstrates a confluent endothelium. Nuclei counterstained by DAPI (blue), scale bar, 250 µm. (e) Co-staining of vWF and α-SMA demonstrate that endothelial layer covers the lumen of the neo-artery and smooth muscle cells occupy the vessel wall, scale bar, 100 µm. (f) Transmission electron microscopy indicates a clear basement membrane (arrowheads) separating endothelial (EC) from smooth muscle cells (SMC), which correlates with the co-staining results of EC and SMC. Scale bar, 20 µm.

FIG. 7 illustrates heparin coating likely allows the grafts to maintain an open porous structure for cell infiltration at 3 days. (a) SEM shows that most of the pores in the graft were occupied, scale bar, 100 µm. (b) Higher magnification reveals that blood cells infiltrate into the pores. No distinguishable fibrin clot has been observed. Scale bar, 10 µm. (c) DAPI staining shows nucleated cells infiltrated into the grafts, scale bar, 250 µm. (d) H&E staining confirms infiltration of nucleated cells in the graft wall. Note that the cells in the lumen have flat elongated nuclei. Scale bar, 50 µm.

Figure 8:
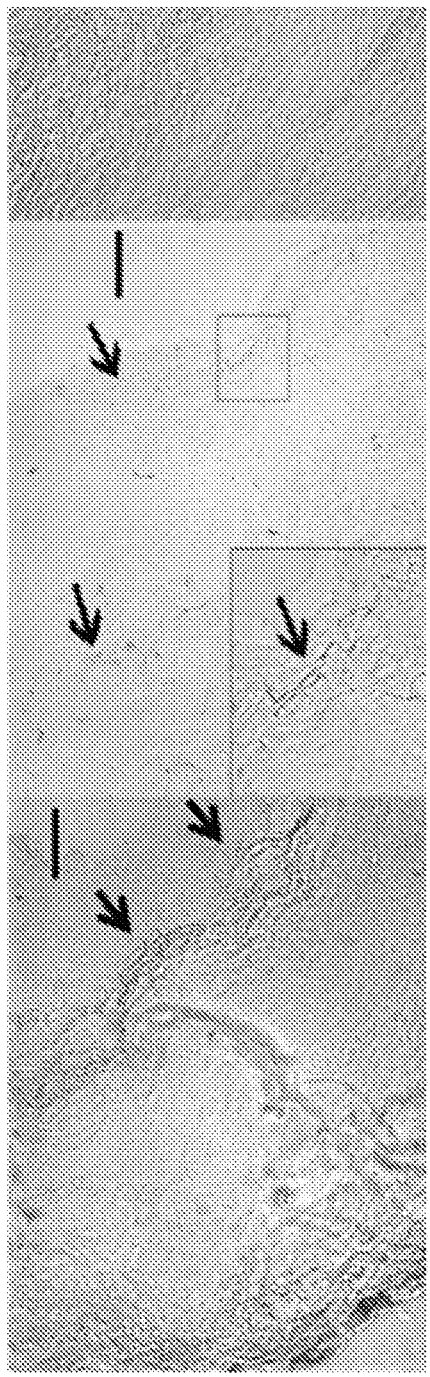

FIG. 8 are bright-field photomicrographs of unstained tissues indicate potential presence of graft materials (arrows). The amount of the putative graft remnants decreases rapidly and is mostly degraded by day 90. All images are 200×, scale bar, 50 µm, inset in 28-day image is 400×.

Figures 9A, 9B:
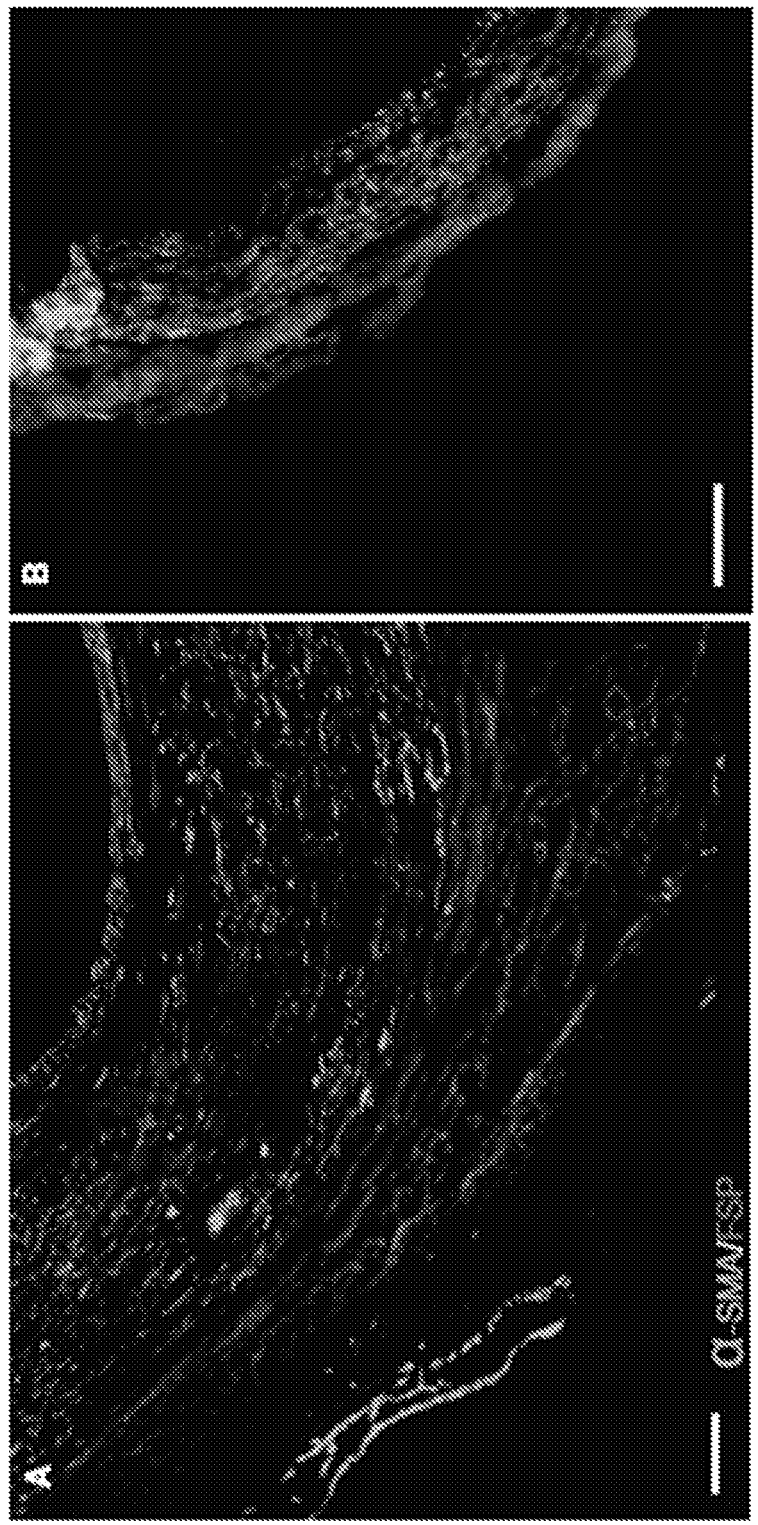

FIG. 9 illustrate neo-arteries have an adventitia-like outer layer populated by fibroblasts at 90 days. (a) Neo-arteries stain positive for fibroblast surface protein (FSP, red) in the outermost layer of the vessel wall. α-SMA co-stain (green) shows a clear boundary between fibroblast and smooth muscle populated layers, similar to that seen in the native aorta shown in (b). Scale bar: 100 µm.

FIG. 10 shows examination of an occluded composite graft at 90 days post implantation. (a) Gross appearance of the occluded graft. (b) Cross-section of graft showed a collapsed lumen. Low magnification, scale bar: 500 µm. (c) H&E staining of occluded graft, scale bar: 200 µm. (d) Boxed region shows irregular cellular arrangement, and the graft appears largely unremodeled, scale bar: 50 µm.

FIG. 11 show PCL grafts are much more limited remodeling in 90 days. (a) Immunofluorescent staining indicates a thin layer of smooth muscle cells (α-SMA) near the graft lumen. Graft split longitudinally, image merged from 100× photomicrographs. (b) Co-staining of endothelial cells (vWF) and smooth muscle cells reveals an endothelial lining over the thin layer of smooth muscle. DAPI nuclei stain demonstrates penetration of nucleated cells in the graft wall. However the cells are not smooth muscle cells. 200×, scale bar, 50 µm. (c) Cross-sectional view of the graft confirms a thin smooth muscle layer near the lumen. Merged from 100× images, scale bar, 250 µm.

FIG. 12 show PCL grafts have limited remodeling in 90 days. (a) Graft is stiff and not integrated with host tissue as indicated by the clear distortion of the graft segment in the aorta. (b) Cross-sectional view of the graft shows layers of cells in the lumen and albumen (outer surface). Nucleated cells are present within graft wall. (c) Verhoeff-van Gieson staining indicates the presence of small amounts of elastin (black). (d) A small amount of collagen III is visible near the lumen. (e) The expression of collagen I is the most extensive among the ECM proteins and spans the lumen to the albumen. Collagen I deposition appears to be associated with nucleated cells in the graft wall. Coupling this with the "walled-off" appearance of the graft in H&E staining suggests that collagen I might serve to isolate the PCL from the host. (f) Elastin anti-body staining shows a low amount of elastin expression mostly near the lumen. All immunofluorescent images are 200×, scale bar, 50 µm.

DETAILED DESCRIPTION OF SEVERAL EMBODIMENTS

I. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example." Although methods and materials similar or equivalent to those described herein can be used in the practice or testing of this disclosure, suitable methods and materials are described below. In addition, the materials, methods, and examples are illustrative only and not intended to be limiting.

In order to facilitate review of the various embodiments of this disclosure, the following explanations of specific terms are provided:

Anticoagulant: A substance that prevents the clotting of blood (coagulation). Anticoagulants are commonly administered to subjects to prevent or treat thrombosis. Generally, anticoagulants are administered to treat or prevent deep vein thrombosis, pulmonary embolism, myocardial infarction, stroke, and mechanical prosthetic heart valves. Various types of anticoagulants with different mechanisms of action are available including anticoagulants that inhibit the effect of vitamin K (such as coumadin) or thrombin directly (such as argatroban, lepirudin, bivalirudin, and ximelagatran) or that activate antithrombin II that in turn blocks thrombin from clotting blood (such as heparin and derivative substances thereof).

Biocompatible: A term describing something that can be substantially non-toxic in the in vivo environment of its intended use, and is not substantially rejected by the patient's physiological system (e.g., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of subjects, will not cause a significantly adverse reaction or response. Furthermore, biocompatibility can be affected by other contaminants such as prions, surfactants, oligonucleotides, and other agents or contaminants. The term "biocompatible material" refers to a material that does not cause toxic or injurious effects on a tissue, organ, or graft.

Biodegradable polymer: A polymer that can be cleaved either enzymatically or hydrolytically to break it down sufficiently so as to allow the body to absorb or clear it away. A biodegradable graft is a graft in which at least a significant portion (such as at least 50%) of the graft degrades within one year of implantation.

Cell-free graft: A graft which does not contain cells, such as, endothelial or smooth muscle cells at the time of implantation.

Coat: As used herein "coating", "coatings", "coated" and "coat" are forms of the same term defining material and process for making a material where a first substance or substrate surface is at least partially covered or associated with a second substance. Both the first and second substance are not required to be different. Further, when a surface is "coated" as used herein, the coating may be effectuated by any chemical or mechanical bond or force, including linking agents. The "coating" need not be complete or cover the entire surface of the first substance to be "coated". The "coating" may be complete as well (e.g., approximately covering the entire first substance). There can be multiple coatings and multiple substances within each coating. The coating may vary in thickness or the coating thickness may be substantially uniform. Coatings contemplated in accordance with the present disclosure include, but not limited to medicated coatings, drug-eluting coatings, drugs or other compounds, pharmaceutically acceptable carriers and combinations thereof, or any other organic, inorganic or organic/inorganic hybrid materials. In an example, the coating is a thromboresistant coating which has anticoagulant properties, such as heparin.

Electrospinning: A process in which fibers are formed from a solution or melt by streaming an electrically charged solution or melt through an orifice.

Poly(caprolactone)(PCL): A biodegradable polyester with a low melting point of around 60° C. and a glass transition temperature of about −60° C. PCL is prepared by ring opening polymerization of ε-caprolactone using a catalyst such as stannous octoate. PCL is degraded by hydrolysis of its ester linkages in physiological conditions (such as in the human body) and can be used as an implantable biomaterial. In some example, PCL is used as a sheath around a PGS scaffold.

Poly(glycerol sebacate)(PGS): An elastomeric biodegradable polyester. In some examples, a disclosed vascular graft includes a PGS scaffold.

Scaffold: A structural support facilitating cell infiltration and attachment in order to guide vessel growth. As disclosed herein, a biodegradable scaffold can be used to form a vascular graft. In some examples, a biodegradable scaffold includes a biodegradable polyester tubular core and a biodegradable polyester electrospun outer sheath surrounding the biodegradable polyester tubular core.

Sheath: An outer coating surrounding either partially or completely an inner layer. As disclosed herein, a sheath surrounds either partially or completely the biodegradable polyester tubular core of a disclosed vascular graft.

Subject: Living multi-cellular vertebrate organisms, a category that includes human and non-human mammals (such as laboratory or veterinary subjects). In an example, a subject is a human. In an additional example, a subject is selected that is in need of an implant for damaged or defective neo-artery.

Vascular graft: A tubular member which acts as an artificial vessel. A vascular graft can include a single material, a blend of materials, a weave, a laminate or a composite of two or more materials.

II. Biodegradable Scaffolds

Disclosed herein are scaffolds, such as tissue engineering scaffolds, including for the replacement and/or repair of damaged native tissues. Although the present disclosure illustrates in detail the use of a disclosed scaffold within a vascular graft, it is contemplated that a disclosed scaffold can be utilized for additional in situ tissue engineering applications, including, but not limited to bone, intestine, liver, lung, or any tissue with sufficient progenitor/stem cells. In some examples, a scaffold is biodegradable and/or biocompatible and includes a biodegradable core, such as a biodegradable polyester tubular core for a vascular graft. In some examples, the biodegradable polyester tubular core includes PGS. In some examples, the biodegradable polyester tubular core includes PGS and one or more biodegradable substances similar to PGS, such as a polymer or an elastomer with relatively fast degradation rate (as described in detail below). These may include derivatives of polyglycolic acid, polycarbonate, polyurethane, polyethylene glycol, and poly(orthoester). It is contemplated that a disclosed graft may include PGS or any biodegradable and/or biocompatible substance with similar degradation rates and elasticity of PGS. In some examples, a disclosed scaffold includes PGS and/or one or more of the following polymers: polylactides (PLAs), poly(lactide-co-glycolides) (PLGAs), poly(dioxanone), polyphosphazenes, polyphosphoesters (such as, poly[1,4-bis(hydroxyethyl)terephthalate-alt-ethyloxyphosphate]; poly[1,4-bis(hydroxyethyl)terephthalate-alt-ethyloxyphosphate]-co-1,4-bis(hydroxyethyl)terephthalate-co-terephthalate; poly[(lactide-co-ethylene glycol)-co-ethyloxyphosphate]); polycaprolactone; poly(urethanes), polyglycolides (PGA) polyanhydrides, and polyorthoesters or any other similar synthetic polymers that may be developed that are biologically compatible. The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated by reference as if set forth fully herein.

In some embodiments, grafts, such as vascular grafts, which are biodegradable and/or biocompatible are disclosed. For example, a vascular graft can include a disclosed biodegradable scaffold with a biodegradable polyester core, such as a biodegradable polyester tubular core for a vascular graft. In some examples, the biodegradable polyester tubular core includes PGS. In some examples, the biodegradable polyester tubular core includes PGS and one or more biodegradable substances similar to PGS, such as a polymer or an elastomer with relatively fast degradation rate (as disclosed herein). These may include derivatives of polyglycolic acid, polycarbonate, polyurethane, polyethylene glycol, and poly(orthoester).

In some examples, a disclosed scaffold/graft includes one or more natural polymers including, but are not limited to amino acids, peptides, denatured peptides such as gelatin from denatured collagen, polypeptides, proteins, carbohydrates, lipids, nucleic acids, glycoproteins, minerals, lipoproteins, glycolipids, glycosaminoglycans, and proteoglycans. In certain embodiments, collagen is included. In certain embodiments, collagen is excluded. In certain cases, non-living macromolecular structures derived from biological tissues including, but are not limited to skins, vessels, intestines, internal organs, can be used alone or in combination with synthetic polymers named above.

In some examples, the scaffold or graft includes pores to facilitate cell infiltration, but pores are not necessarily required. In examples in which pores are built into the scaffolds or grafts, the pore size can range from 2 to 500 microns (µm). In some examples, the biodegradable polyester core, such as a biodegradable polyester tubular core, comprises pores of about 1 µm to about 500 µm, from about 10 µm to about 400 µm, about 20 µm to about 300 µm, about 1 µm to about 10 µm, about 3 µm to about 7 µm, such as 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, or 500 µm. In some examples, pores are about 20 µm to about 30 µm, including about 20 µm, 21 µm, 22 µm, 23 µm, 24 µm, 25 µm, 26 µm, 27 µm, 28 µm, 29 µm, and 30 µm. In some examples, the pores are uniformly distributed. In some examples, the pores are non-uniformly distributed. In some examples, the biodegradable polyester tubular porous core has at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

In some examples, the biodegradable scaffold further includes a sheath which surrounds the biodegradable polyester tubular core. In some examples, the sheath is a biodegradable polyester electrospun sheath which surrounds the biodegradable polyester tubular core to prevent, inhibit or reduce bleeding from such graft. In some examples, the biodegradable polyester electrospun sheath includes PCL or a PCL like substance which is capable of forming a leak-proof sheath around the biodegradable polyester electrospun sheath. In some examples, a biodegradable scaffold does not include a sheath. For example, a biodegradable scaffold includes one or more biodegradable polyesters or like substances without a sheath. In one particular example, a biodegradable scaffold includes PGS and one or more carrier polymers, such as such as poly(lactic acid) (PLA), poly-caprolactone (PCL) or poly(glycolic acid) (PGA), and/or the copolymer poly(lactide-co-glycolide) (PLGA).

In one particular example, the biodegradable scaffold includes a PGS core surrounded by an electrospun PCL sheath.

In some examples, the sheath has a thickness between about 5 μm and 30 lam, such as between about 10 μm and about 20 μm, including 10 μm, 11 μm, 12 μm, 13 μm, 14 μm, 15 μm, 16 μm, 17 μm, 18 μm, 19 μm, 20 μm, 21 μm, 22 μm, 23 lam, 24 μm, 25 μm, 26 μm, 27 μm, 28 μm, 29 μm, and 30 μm. In one example, the biodegradable polyester electrospun outer sheath has a thickness of about 15 μm.

In some examples, the biodegradable scaffold is coated with a biocompatible and/or biodegradable material. It is contemplated that one of ordinary skill in the art can determine with but limited experimentation, which substrates are suitable for a particular application. In some examples, the inner luminal surface of the biodegradable scaffold is coated with a biocompatible and/or biodegradable material. It is contemplated that such coating may be complete or partial. In some examples, the inner luminal surface of a biodegradable scaffold is coated completely with a thromboresistant agent, such as heparin and/or other compounds known to one of skill in the art to have similar anti-coagulant properties as heparin, to prevent, inhibit or reduce clotting within the inner lumen of the vascular graft.

In some examples, the scaffold can be impregnated with any of a variety of agents, such as, for example, suitable growth factors, stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), hepatocyte growth factor (HGF), stromal cell derived factor (SDF), platelet derived growth factor (PDGF), keratinocyte growth factor (KGF), skeletal growth factor (SGF), osteoblast-derived growth factor (BDGF), insulin-like growth factor (IGF), cytokine growth factor (CGF), stem cell factor (SCF), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), interferon, interleukins, cytokines, integrin, collagen, elastin, fibrillins, fibronectin, laminin, glycosaminoglycans, heparan sulfate, chondrotin sulfate (CS), hyaluronic acid (HA), vitronectin, proteoglycans, transferrin, cytotactin, tenascin, and lymphokines.

The various dimensions of a disclosed scaffold or graft may vary according to the desired use. In principle, the dimensions will be similar to those of the host tissue in which the scaffold/graft is being used to replace. For examples, the inner diameter of a vascular graft will match that of the host vessel to be replaced. In some examples, the inner diameter is between about 1 mm to 5 mm. In some examples, a disclosed vascular graft has an inner diameter of between about 700 μm to about 5000 μm, such as about 710 μm to about 4000 μm, such as about 720 μm to about 3000 μm, such as about 1000 μm to about 5000 μm, including 710 μm, 711 lam, 712 μm, 713 μm, 714 μm, 715 μm, 716 μm, 717 μm, 718 μm, 719 μm, 720 lam, 721 μm, 722 μm, 723 μm, 724 μm, 725 μm, 726 μm, 727 μm, 728 μm, 729 lam, 730 μm, 731 μm, 732 μm, 733 μm, 734 μm, 735 μm, 736 μm, 737 μm, 738 lam, 739 μm, 740 μm, 741 μm, 742 μm, 743 μm, 744 μm, 745 μm, 746 μm, 747 μm, 748 μm, 749 μm, 750 μm, 800 μm, 850 μm, 900 μm, 950 μm, 1000 μm, 2000 lam, 3000 μm, 4000 μm or 5000 μm. In some examples, the inner diameter of a disclosed vascular graft is about 720 μm. In some examples, the inner diameter of a disclosed vascular graft is about 1000 μm. In some examples, the inner diameter of a disclosed vascular graft is about 2000 μm. In some examples, the inner diameter of a disclosed vascular graft is about 3000 μm.

Typically, the wall thickness of a disclosed scaffold or vascular graft is designed to match that of the host tissue or vessel to be replaced. However, it is contemplated the graft can be thicker or thinner, if desired. In some examples, a disclosed vascular graft has a wall thickness between about 100 μm and about 500 μm, such as about 150 μm and about 450 μm, including about 200 μm and about 400 μm, such as about 100 μm, 125 μm, 150 μm, 175 μm, 200 μm, 225 μm, 250 lam, 275 μm, 300 μm, 325 μm, 350 μm, 375 μm, 400 μm, 425 μm, 450 μm, 475 lam, or 500 μm. In some examples, a disclosed vascular graft has a wall thickness between about 270 μm and about 300 μm, such as about 285 μm and about 295 μm, including 270 μm, 271 μm, 272 μm, 273 μm, 274 μm, 275 μm, 276 μm, 277 μm, 278 μm, 279 μm, 280 μm, 281 μm, 282 μm, 283 μm, 284 μm, 285 μm, 286 μm, 287 μm, 288 μm, 289 μm, 290 μm, 291 μm, 292 μm, 293 μm, 294 μm, 295 μm, 296 μm, 297 μm, 298 μm, 299 μm, or 300 μm. In some examples, the wall thickness is about 290 μm.

In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within one year of implantation, such as within 1 to 10 months, including within 1 month, 2 months, 3 months, 4 months, 5 months, 6 months, 7 months, 8 months, 9 months, 10 months, 11 months or 12 months of implantation. In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within 2 weeks to 52 weeks of implantation, including within 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, or 52 weeks of implantation.

In some examples, about 80% to about 95% of the graft degrades within 4 weeks. In some examples, about 80% to about 95% of the graft degrades within 6 weeks. In some examples, about 80% to about 95% of the graft degrades within 8 weeks. In some examples, about 80% to about 95% of the graft degrades within 10 weeks. In some examples, about 80% to about 95% of the graft degrades within 14 weeks. In some examples, about 80% to about 95% of the graft degrades within 16 weeks. In some examples, about 80% to about 95% of the graft degrades within 18 weeks. In some examples, about 80% to about 95% of the graft degrades within 20 weeks. In some examples, about 80% to about 95% of the graft degrades within 22 weeks. In some examples, about 80% to about 95% of the graft degrades within 24 weeks. In some examples, about 80% to about 95% of the graft degrades within 26 weeks.

In some examples, at least 90% of the graft degrades within 4 weeks. In some examples, at least 90% of the graft degrades within 6 weeks. In some examples, at least 90% of the graft degrades within 8 weeks. In some examples, at least 90% of the graft degrades within 10 weeks. In some examples, at least 90% of the graft degrades within 12 weeks. In some examples, at least 90% of the graft degrades within 14 weeks. In some examples, at least 90% of the graft degrades within 16 weeks. In some examples, at least 90% of the graft degrades within 18 weeks. In some examples, at least 90% of the graft degrades within 20 weeks. In some examples, at least 90% of the graft degrades within 22 weeks. In some examples, at least 90% of the graft degrades within 24 weeks. In some examples, at least 90% of the graft degrades within 26 weeks.

In some examples, at least 95% of the graft degrades within 4 weeks. In some examples, at least 95% of the graft degrades within 6 weeks. In some examples, at least 95% of the graft degrades within 8 weeks. In some examples, at least 95% of the graft degrades within 10 weeks. In some examples, at least 95% of the graft degrades within 12 weeks. In some examples, at least 95% of the graft degrades within 14 weeks. In some examples, at least 95% of the graft degrades within 16 weeks. In some examples, at least 95% of the graft degrades within 18 weeks. In some examples, at least 95% of the graft degrades within 20 weeks. In some examples, at least 95% of the graft degrades within 22 weeks. In some examples, at least 95% of the graft degrades within 24 weeks. In some examples, at least 95% of the graft degrades within 26 weeks.

In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within 4 weeks of implantation, such as within 1 week, 2 weeks, 3 weeks and 4 weeks.

In some examples, a disclosed scaffold/graft, such as a disclosed vascular graft, is cell-free, in which it does not include any living cells, such as smooth muscle cells or endothelial cells.

III. Methods of Fabrication

Also disclosed herein are methods of fabricating a scaffold or graft, such as a vascular graft. A disclosed scaffold or graft may be fabricated by methods known to those of skill in the art. In some embodiments, a method of fabricating a scaffold or graft, such as a vascular graft, which is biodegradable and/or biocompatible comprises preparing a biodegradable polyester core (such as a tubular core for a vascular graft) and surrounding the biodegradable polyester core with a sheath. In some examples, a disclosed scaffold or graft is prepared by using salt fusion and leaching or electroprocessing, such as electrospinning. In particular examples, the method includes synthesizing the biodegradable polyester material and then forming a core, such as a tubular core, with such material. The biodegradable polyester material can be synthesized by any method known to one of skill in the art to generate the material with desired properties, including, but not limited to, a desired shape, thickness, porosity, fiber strength, or elasticity. For example, PGS can be first synthesized by any method known to one of ordinary skill in the art, including, but not limited to, the method described in Wang et al. (*Nat. Biotechnol.* 20:602-606, 2002) which is hereby incorporated by reference in its entirety). The synthesized biocompatible and biodegradable polyester material can then formed into the desired shape by use of any method known to one of ordinary skill in the art. In some examples, the biodegradable and biocompatible polyester material is shaped based upon the shape of the structure, such as a blood vessel, the resulting vascular graft is replacing. In some examples, a PGS tube is formed by the method described in Lee et al. (*Proc Natl Acad Sci USA* 108: 2705-2710, 2011) which is hereby incorporated by reference in its entirety except that a 1 mm mandrel and a 1.25 mm outer mold is used.

In some examples, the biodegradable scaffold or biodegradable core, such as tubular core, is fabricated to comprise pores of about 1 µm to about 500 µm, from about 10 µm to about 300 µm, about 20 µm to about 300 µm, about 1 µm to about 10 µm, about 3 µm to about 7 µm, such as 1 µm, 2 µm, 3 µm, 4 µm, 5 µm, 6 µm, 7 lam, 8 µm, 9 µm, 10 µm, 11 µm, 12 µm, 13 µm, 14 µm, 15 µm, 16 µm, 17 µm, 18 lam, 19 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, or 500 µm. In some examples, pores are about 20 µm to about 30 µm, including about 20 µm, 21 µm, 22 lam, 23 µm, 24 µm, 25 µm, 26 µm, 27 µm, 28 µm, 29 µm, and 30 µm. In some examples, the biodegradable scaffold or core is fabricated to include uniformly distributed pores. In some examples, the biodegradable polyester scaffold or core is fabricated to include non-uniformly distributed pores. In some examples, the biodegradable scaffold is fabricated to not include pores.

In some examples, the biodegradable polyester tubular porous core is fabricated to include at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

In some examples, sheath is fabricated to surround the biodegradable polyester core, such as tubular core, by electrospinning. For example, a PCL sheath is formed around a PGS or like composition core by electrospinning PCL onto a PGS core, such as PGS-salt template (as described in the Examples below). In some examples, the sheath is fabricated to have a thickness between about 5 µm and 30 µm, such as between about 10 µm and about 20 µm, including 10 µm, 11 µm, 12 lam, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, and 30 µm. In one example, the biodegradable polyester electrospun outer sheath has a thickness of about 15 µm.

In further examples, the disclosed methods of fabrication include coating a surface of the biodegradable scaffold, such as a surface of a biodegradable polyester tubular core with a biocompatible and/or biodegradable material. It is contemplated that one of ordinary skill in the art can determine with but limited experimentation, which substrates are suitable for a particular application. In some examples, the inner luminal surface of the biodegradable scaffold is coated with a biocompatible and/or biodegradable material. It is contemplated that such coating may be complete or partial. In some examples, the inner luminal surface of a biodegradable scaffold is coated completely with a thromboresistant agent, such as heparin and/or other compounds known to one of skill in the art to have similar anti-coagulant properties as heparin, to prevent, inhibit or reduce clotting within the inner lumen of the vascular graft.

The various dimensions of a disclosed graft may vary according to the desired use. In some examples, the method of fabrication is performed to generate a vascular graft with an inner diameter which matches that of the host vessel to be replaced. In some examples, the inner diameter is between about 1 mm to 5 mm. In some examples, a disclosed vascular graft has an inner diameter of between about 700 µm to about 5000 µm, such as about 710 µm to about 4000 µm, such as about 720 µm to about 3000 µm, such as about 1000 µm to about 5000 µm, including 710 µm, 711 µm, 712 µm, 713 µm, 714 µm, 715 µm, 716 µm, 717 µm, 718 µm, 719 µm, 720 µm, 721 µm, 722 µm, 723 µm, 724 µm, 725 µm, 726 µm, 727 µm, 728 µm, 729 µm, 730 µm, 731 µm, 732 µm, 733 µm, 734 µm, 735 µm, 736 µm, 737 µm, 738 µm, 739 µm, 740 µm, 741 µm, 742 µm, 743 µm, 744 µm, 745 µm, 746 µm, 747 µm, 748 µm, 749 µm, 750 µm, 800 µm, 850 µm, 900 µm, 950 µm, 1000 µm, 2000 µm, 3000 µm, 4000 µm or 5000 µm. In some examples, the inner diameter of a disclosed vascular graft is fabricated to be about 720 µm. In some examples, the inner diameter of a disclosed vascular graft is fabricated to be about 1000 µm. In some examples, the inner diameter of a disclosed vascular graft is about fabricated to be about 2000 µm. In some examples, the inner diameter of a disclosed vascular graft is fabricated to be about 3000 µm.

In some examples, the method of fabrication is performed to generate a vascular graft with a wall thickness which matches that of the host vessel to be replaced. However, it is contemplated the graft wall can be fabricated with a thicker or thinner wall than that which is being replaced, if desired. In some examples, a disclosed vascular graft is fabricated to have a wall thickness between about 100 µm and about 500 µm, such as about 150 µm and about 450 µm, including about 200 µm and about 400 µm, such as about 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, or 500 µm. In some examples, a disclosed vascular graft is fabricated to have a wall thickness between about 270 µm and about 300 µm, such as about 285 µm and about 295 µm, including 270 µm, 271 µm, 272 µm, 273 µm, 274 µm, 275 µm, 276 µm, 277 µm, 278 µm, 279 µm, 280 µm, 281 µm, 282 µm, 283 µm, 284 µm, 285 µm, 286 µm, 287 µm, 288 µm, 289 µm, 290 µm, 291 µm, 292 µm, 293 µm, 294 µm, 295 µm, 296 µm, 297 µm, 298 µm, 299 µm, or 300 µm. In some examples, the wall thickness is about 290 µm.

In some examples, the method of fabrication are performed to generate a scaffold/graft such as a vascular graft that at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of such scaffold/graft degrades within one year of implantation, such as within one three months, four months, five months, six months, seven months, eight months, nine months, ten months, eleven months or twelve months.

In some examples, the method of fabrication includes generating a cell-free scaffold/graft, such as a cell-free vascular graft, in which the graft does not include any living cells, such as smooth muscle cells or endothelial cells.

IV. Methods of Use

It is contemplated that the disclosed scaffolds/grafts can be used to guide host tissue remodeling in many different tissues, including any tissue that has progenitor cells. The disclosed biodegradable scaffolds can be used to facilitate tissue regeneration in vivo by providing a structural frame for which tissue regeneration can occur. In some examples, the scaffolds/grafts or constructed to allow and facilitate the infiltration of host cells including progenitor cells. In some examples, the scaffolds/graft allows and facilitates host remodeling of the biodegradable structure, so that eventually the polymeric structure is replaced by the desirable host tissue. It is contemplated that the methods of fabrication disclosed in Section III and the Examples below can be modified as desired by one of ordinary skill in the art to fabricate a graft with the appropriate dimensions and features depending upon tissue which is to be replaced.

The disclosed scaffolds are especially useful for applications in soft and elastomeric tissues. In some particular examples, the generated tissue constructs are for the replacement and/or repair of damaged native tissues. For example, the disclosed constructs are contemplated to be implantable for tensile load bearing applications, such as being formed into tubes and implanted as artery interpositional grafts as well as other tensile load bearing applications. A disclosed scaffold/graft can be utilized for additional in situ tissue engineering applications, including, but not limited to bone, intestine, liver, lung, or any tissue with sufficient progenitor/stem cells. For example, uses can range from sheets for hernia repair, prolapse, and wound dressings, to complex tubes for blood vessel, nerve and trachea repair. Additionally, aligned random transition spinning may be useful for ligament-bone interfaces.

In some particular examples, a biodegradable scaffold comprising a biodegradable polyester core and a biodegradable polyester electrospun outer sheath surrounding the biodegradable polyester core with or without a thromboresistant agent coating the biodegradable scaffold is used to facilitate tissue regeneration in vivo by providing a structural frame for which tissue regeneration can occur.

In some examples, a disclosed vascular graft is used to form a blood vessel in vivo. For example, a disclosed vascular graft can be implanted into a subject in need of vascular graft at the desired location to form a conduit in which blood may initial flow and ultimately form a blood vessel, such as blood vessel of less than 10 mm, such as less than 6 mm or less than 4 mm, including, about 9 mm, about 8 mm, about 7 mm, about 6 mm, about 5 mm, about 4 mm, about 3 mm, about 2 mm, or about 1 mm, or as low as 0.5 mm. In some examples, the vascular graft is used as a coronary or a peripheral arterial graft or venous grafts or lymphatic vessels. In some examples, the vascular graft is used as an arteriovenous shunt for dialysis access where "maturation" of 2-3 months is common.

The following examples are provided to illustrate certain particular features and/or embodiments. These examples should not be construed to limit the disclosure to the particular features or embodiments described.

EXAMPLES

Example 1

Material and Methods for Studies Described in Examples 2-4

This example describes the materials and methods used to perform the studies provided in Examples 2-4.

i. Graft Fabrication

A modified salt fusion and leaching method was used to fabricate the PGS core, and an electrospinning technique was used to fabricate the PCL sheath. PGS was synthesized as previously described in Wang et al. (*Nat. Biotechnol.* 20:602-606, 2002) which is hereby incorporated by reference in its entirety. The PGS tube was made as previously described in Lee et al. (*Proc Natl Acad Sci USA* 108: 2705-2710, 2011) which is hereby incorporated by reference in its entirety except that a 1 mm mandrel and a 1.25 mm outer mold was used. PCL ($M_n$ 80 kDa, Aldrich, St. Louis, Mo.) was dissolved in 2,2,2-trifluoroethanol (ACROS, Geel, Belgium) to obtain a 14% w/v solution, and electrospun onto the rotating PGS-salt template (20 rpm). The PCL-PGS-salt composites were immersed in deionized water to remove the salt. The porous grafts were freeze-dried in a lyophilizer (Labconco Freezone 4.5). The grafts were stored dry in a desiccator at ambient temperature. Ethylene oxide sterilization was performed before graft implantation.

ii. Graft Characterization

SEM.

The grafts were cut into 3 mm long segments and their luminal surfaces and cross-sections were examined. All sections were mounted onto an aluminum stub with carbon tape, sputter-coated with gold, and observed by a field emission SEM (6330F, JEOL) at 5-kV accelerating voltage.

Micro-CT.

Inner diameter and wall thickness of each graft were obtained by morphometric analysis using a benchtop cone beam micro-CT system (μCT 40, Scanco Medical) with a microfocus X-ray (6 μm of isotropic voxel size, E=45 kVp, and integration time=300 ms with 3× frame averaging) as previously described in Lee et al. (*Proc Natl Acad Sci USA* 108: 2705-2710, 2011). A total of 200-250 slices were acquired for each graft section, and images were binarized by applying a Gaussian noise reduction filter with fixed threshold. Raw data were reconstructed to 2D tomograms using an automatic convolution back-projection algorithm. Average pore size and strut thickness were computed by using the direct distance transformation method and averaging them for material and pore diameters measured over the entire 3D volume. Surface area to volume ratio was calculated by dividing measured surface area into PGS object volume. Pore interconnectivity was assessed by inverting the solid and pore spaces, eliminating any disconnected closed pores, and determining the percentage of connected pore space to total pore volume. Three-dimensional morphometric parameters as well as thickness and separation distribution maps were generated.

Mechanical Testing.

Elastic modulus and suture retention strength of the grafts were determined by an electromechanical testing machine (Insight, MTS Systems, Eden Prairie, Minn.) equipped with a 5.0 N load cell. To measure tensile strength and elastic modulus, grafts were cut into 2-mm long segments (Composite PGS-PCL grafts: n=8, PGS-only grafts n=3). All segments were fixed to two identical hooks connected to the load cell and the bottom plate of machine. Uniaxial tensile force was applied to each segment at a rate of 0.01 mm/s. Segments were first preconditioned between 10 and 40% ring strain until reproducible stress-strain curves were obtained. Strain to failure was then performed. Cauchy stress, circumferential strain, and elastic modulus were calculated. Ultimate tensile strength was taken as the peak stress of the stress-strain curve.

Suture retention strength was measured on five samples by placing a 7-0 prolene suture approximately 1 mm from the end of the graft. The suture was fixed into the upper hook with the graft immobilized in the lower hook. The force needed to pull the suture apart from the graft was measured using a crosshead speed of 2 mm/min. As a control, break forces of 9-0 sutures were measured to evaluate whether the suture retention met the microsurgical requirement.

iii. Animal Studies

Implantation.

Male Lewis rats (body weight: 200-250 g, Charles River Laboratories, Boston, Mass.) were used for animal studies. A total of 27 rats were successfully implanted with either the PGS based composite grafts (n=21) or porous grafts made completely from PCL (n=6). Surgical survival rate was 87.5% (21/24). Three rats died during surgery due to bleeding from aortic or inferior vena cava injury, and these were excluded from animal counts. Vascular grafts implantation procedure in rat abdominal aorta. Briefly, the rat was anesthetized by isoflurane inhalation and a midline incision was performed on abdominal skin under standard sterile conditions. The abdominal aorta was exposed and separated carefully from accompanying inferior vena cava. The infrarenal abdominal aorta was cross-clamped and a 4 mm segment was transected and the vascular graft (8-10 mm in length) was inserted into the aorta gap. End to end anastomosis technique was used to connect the graft with native aorta using 9-0 nylon sutures. After confirmation of patent blood flow in grafts and no bleeding post de-clamping, the wound was closed. The animals were allowed to recover from surgery and maintained without anti-coagulation or anti-platelet treatment postoperatively. At 14 days (n=5), 28 days (n=5) and 90 days (n=11) post-implantation, rats were sacrificed and grafts were explanted for analysis. All rats implanted with PCL-only grafts (n=6) were sacrificed at 90 days.

X-Ray Angiography and Doppler-Ultrasound Examination.

For the examination of graft patency during the remodeling process, Doppler-ultrasound examination was performed monthly in rats to detect arterial blood flow in grafts. Additionally, X-ray angiography was performed before grafts were harvested. Briefly, the rat was heparinized by administrating 0.5 ml heparin solution (2 mg/ml) via intracardiac injection after sacrifice. Contrast agent (Iopamidol, Isovue 370) was injected into the thoracic aorta before X-ray images were acquired.

iv. Histology

Explanation and Staining.

Explanted grafts were embedded in OCT, frozen at −80° C. for 2 hours, cryosectioned into slides of 8 μm thicknesses. The slides were fixed in 10% (vol/vol) formalin and dehydrated serially in ethanol. Sections were stained with H&E, Verhoeff-van Gieson (VGG), Masson's trichrome (MTS) and Safranin-O stains. Images were captured with an inverted microscope (Eclipse Ti-E, Nikon Instruments Inc, Japan) and analyzed by Nikon NIS-Elements software. All histological images are representative of at least 6 independent samples from 3 rats studied.

Luminal Area Measurement.

To quantify luminal area of the grafts, cryosections from 3 different 13-week grafts (2 cryosections each graft) were stained with H&E, images were merged from 100× brightfield micrographs, and the luminal area of tissue ring was measured using Nikon NIS Element Software. As controls, native abdominal aorta (3 explants×2 sections) from age-matched healthy Lewis rats were harvested and processed identically.

SEM.

The harvested grafts were rinsed with PBS and fixed with 2.5% glutaraldehyde for 4 hours. After dehydration in ascending series of ethanol, critical point drying was completed by replacing 100% ethanol with hexamethyldisilazane (Aldrich) in a series of baths (75:25, 50:50, 25:75, and three times 0:100) for 15 min each. Dried samples were mounted onto an aluminum stub with carbon tape, sputter-coated with gold, and observed by SEM at 5-kV accelerating voltage.

TEM.

The harvested grafts were cut into small rings of about 1 mm width and rinsed in PBS. The samples were fixed by 2.5% glutaraldehyde and underwent serial dehydration and embedded into the Epon. Sections were cut from embedded samples and stained with toluidine blue and basic fuchsine. After screening stained slides with light microscope, areas of interest were selected for ultrathin sectioning and stained with uranyl acetate and lead citrate and examined in a JEM 1210 Electron Microscope.

v. Immunofluorescence Staining

Cryosections (8-μm thick) cut from neo-arteries and native rat aortas were dried, fixed in cold acetone for 15 min, air-dried, and rinsed twice with PBS. Slides were incubated with 5% normal goat serum (Sigma) for 1 hour at 37° C., incubated with primary antibodies in 1% goat serum for 45 minutes at 37° C., rinsed twice with PBS, incubated with secondary antibody in 1% goat serum for 45 minutes at 37° C., and rinsed twice with PBS and once with deionized $H_2O$. For α-smooth muscle actin (SMA) staining, FITC-conjugated mouse monoclonal anti-rat SMA (1:400, Sigma) was used as a primary antibody. For myosin-heavy chain (MHC) staining, mouse monoclonal anti-rat MHC (1:80, Abcam Inc. Cambridge, Mass.) was used as a primary antibody and Alexa Fluor 594 goat anti mouse IgG (1:400, Invitrogen, Carlsbad, Calif.) was used as a secondary antibody. For fibroblast surface protein (FSP) staining, mouse monoclonal anti-human FSP (1:400, Sigma) was used as a primary antibody and Alexa Fluor 594 goat anti mouse IgG (1:400, Invitrogen) was used as a secondary antibody. Nuclei were stained with DAPI (bisbenzamide 1 mg/100 ml) for 30 minutes.

Fluorescent images were captured with an inverted microscope (Eclipse Ti-E, Nikon Instruments Inc.). For elastin and collagen staining, cryosections (8-μm thick) were prepared with the same procedure mentioned above. Slides were incubated with rabbit polyclonal anti-rat elastin (1:80, Abcam Inc.), or rabbit polyclonal anti-rat Collagen I, III (1:100, Abcam Inc.) as primary antibodies for 40 minutes at 37° C., slides were then washed three times with PBS solution and incubated for 40 min at room temperature with a secondary antibody goat anti-rabbit (1:1000, Jackson ImmunoResearch Laboratories Inc. West Grove, Pa.) and Alexa Fluor 594-goat anti-mouse IgG (1:400, Invitrogen) respectively. After three rinses with PBS, sections were coverslipped with Gelvatol mounting media. Fluorescent images were captured with a laser scanning confocal microscope (Fluoview FV500, America Inc. Center Valley, Pa.). Tissue slides pretreated without primary antibody only were used as negatives, and rat aorta arteries were used as positive controls. All immunofluorescence images are representative of at least 6 independent samples from 3 rats studied.

Inflammatory cells in the graft wall were evaluated by H&E staining and newly recruited macrophages were immunostained using mouse anti-rat CD68 (1:50, Serotec, Raleigh, N.C.) primary antibody and Alexa Fluor 594 goat anti mouse IgG (1:400, Invitrogen) secondary antibody. CD163+ cells were immunostained using mouse anti-rat CD163 (1:50, Serotec) primary antibody and Alexa Fluor 594 goat anti mouse IgG (1:400, Invitrogen) secondary antibody. Six representative images at 100× were randomly chosen from micrographs of each group, the positively stained cells were counted by Nikon NIS Elements Software. The results showed that the 14-day grafts (865.83±226.02) appeared to have a greater number of macrophages per field in comparison with the 28-day grafts (385.67±216.14), and 90-day grafts showed a significantly diminished amount of inflammatory cells (49.17±64.40) as compared with earlier time points, which indicated no chronic inflammation was triggered by the grafts.

vi. Biochemical Evaluations and DNA Quantification

The elastin content of regenerated and native arteries was quantified using a Fastin Elastin Assay kit (F2000; Biocolor, Carrickfergus, UK). Tissue samples (3-mm long) were harvested from midgrafts and minced into small pieces (approximately 1.0 $mm^3$), weighed, and digested four times with 0.25 mol/l oxalic acid at 95° C. for 1 hour. Elastin concentration in pooled supernatants was measured following kit instruction and insoluble elastin per wet weight of each sample was calculated from the elastin standard curve. For collagen quantification, the tissue obtained as described above was minced into small pieces (approximately 1.0 $mm^3$), weighed and digested with 0.5% acetic acid solutions containing 0.2% pepsin at 4° C. overnight on an orbital shaker. To further dissolve insoluble content in tissues, dissolved remnant was added with deionized water and heated at 80° C. for 30 min. Total collagen was quantified using Sircol™ Collagen Assay (MP Biomedicals, Solon, Ohio). Collagen concentration in pooled supernatants was measured following the kit instruction and collagen quantity per wet weight of each sample was calculated from the standard curve.

To quantify the DNA, frozen explants (n=3 per group) were thawed, minced, and incubated for 6 hours in lysis buffer (Qiagen, Germantown, Md.) and proteinase K (12 mAU/reaction) at 56° C. DNA was isolated from samples using DNeasy Blood and Tissue Kit (Qiagen) following manufacturer's instructions. DNA content was measured by absorbance at 260 nm, then normalized to tissue wet weight.

vii. Mechanical Characterization

Compliance and Tensile Elastic Modulus of Aortic Segments:

Aortic segments (1 cm length) were trimmed of connective tissue, and branching vessels were sealed with 7-0 suture. Aortas were then strained longitudinally to 10% and pressurized by infusing with PSS using a syringe pump (NE-1000, New Era Pump Systems, Farmingdale, N.Y.). Aortas were preconditioned between 0 and 130 mm Hg until pressure vs. diameter curves were reproducible. Compliance and modulus measurements were calculated using the last cycle. Pressure and diameter data were measured using a pressure transducer (PX309 Omegadyne, Sunbury, Ohio) and optical micrometer (LS7070, Keyence, Itasca, Ill.) and synchronously recorded with a data acquisition system (PowerLab 830, ADInstruments, Colorado Springs, Colo.)

Outer diameter was converted to inner diameter for compliance calculations to reduce the effect of variations in the thickness of residual connective tissue on aortas:

$$D_{inner} = \sqrt{D_{outer}^2 - \frac{4(A_{wall})}{\pi}} \quad (1)$$

where $D_{inner}$ represents inner diameter, $D_{outer}$ represents outer diameter, and $A_{wall}$ represents axial cross-sectional area of the vessel wall. $A_{wall}$ is constant under the assumption of incompressible tissue because vessel wall volume must be conserved and the vessel longitudinal dimension is fixed by suture in the testing apparatus. Consequently, $A_{wall}$ can be calculated from the unstretched cross-sectional area $A_{wall,0}$:

$$A_{wall} = A_{wall,0} = \pi * h_0 (D_{outer,0} - h_0) \quad (2)$$

where h represents wall thickness, and the subscript 0 denotes measurement at zero lumenal pressure. $D_{outer,0}$ and $h_0$ were measured from camera images of aortic cross sections.

Compliance was calculated in two forms. First, as a function of pressure (expressed as percent diameter change per 100 mmHg):

$$C = \frac{\frac{D_{innerl}(P_2) - D_{inner}(P_1)}{D_{innerl}(P_1)}}{P_2 - P_1} \times 10^4 \quad (3)$$

where $P_1$ and $P_2$ are the lower and higher pressures, respectively.

Second, as a measure of the percent change in diameter between 80 and 120 mm Hg, with respect to the diameter at 80 mm Hg (expressed as percent).

$$C = \frac{D_{inner}(P_{120}) - D_{inner}(P_{80})}{D_{inner}(P_{80})} \times 100 \quad (4)$$

To determine tensile elastic modulus at physiologic pressures, stress-strain curves were produced from pressure-diameter data using the following equations:

Circumferential Ring Strain:

$$\lambda_{\theta\theta} = \frac{D_{inner}}{D_{inner,o}} \quad (5)$$

Cauchy Stress:

$$\sigma_{\theta\theta} = \frac{P * D_{outer} * \lambda_{\theta\theta}}{h} - P \quad (6)$$

Tensile elastic modulus within the physiologic pressure range was calculated from the slope of stress strain curves between 80 and 120 mm Hg luminal pressure:

$$E = \frac{\sigma_{\theta\theta}(P_{120}) - \sigma_{\theta\theta}(P_{80})}{(P_{120}) - (P_{80})} \quad (7)$$

Compliance was also tested for new PGS-PCL grafts before implantation (n=4), as well as PGS tube without the PCL sheath (n=4). Infusion rate was doubled to compensate for leakage due to high graft porosity. Compliance values are likely an underestimate due to leakage. Consequently, their stress-strain relation and tensile elastic modulus was calculated from uniaxial testing rather than from pressure-diameter data. Burst pressure was determined by pressurizing aortas with PSS until failure. Peak pressure was taken as burst pressure. PGS-PCL grafts and bare PGS tubular core could not be burst due to substantial fluid leakage during testing.

viii. Statistical Analysis

Comparisons between two groups were assessed using a two-tailed Student's t test. Comparisons between three or more groups were made using a one way ANOVA followed by Tukey's HSD post-hoc test. Normal distribution of data and homogeneity of variance between groups were confirmed with IBM SPSS Statistics 19 (Armonk, N.Y.).

Example 2

Characterization of Composite Graft

This example describes the characterization of the composite graft and the overall scheme of its application.

The challenge of arterial substitutes is that among many other criteria, they need to withstand arterial pressure immediately upon implantation and the material needs to bear the load before native matrix is synthesized. The classic approaches to arterial substitutes have always focused on strong materials. This is reflected in autografts, synthetic grafts, and tissue-engineered grafts based on collagen, cell-sheets, poly(hydroxy alkanoate), and decellularized natural or engineered tissues. Tissue-engineered grafts typically exhibit high burst pressure, low compliance, and limited host cell infiltration and remodeling even 6-12 months post-implantation. In vascular extracellular matrix (ECM), collagen provides strength and elastin provides elastic recoil. Collagen expression is typically very high for existing vascular grafts whereas elastin expression is usually low. Host remodeling of tissue engineered constructs post-implantation can increase elastin expression. This positive remodeling indicates that the host may be a good source of cells and a more efficient "bioreactor" than the current in vitro tissue-engineering paradigm. FIG. 1a provides a schematic representation of direct implantation of the cell-free graft and the proposed remodeling process of the graft into a biological neo-artery. Rapid remodeling of a synthetic graft to a neo-artery offers efficient integration with host tissue, a nonthrombogenic lumen, and mechanical properties matching native vessels because it reduces the duration of host exposure to foreign materials. Enabling application of synthetic vascular grafts in small diameter arteries offers multiple advantages: avoidance of donor site morbidity, bypass of in vitro cell culture, ready availability, easy storage and transport, and potentially faster clinical adoption.

To design a synthetic graft capable of rapid host remodeling, the following criteria were examined: (1) graft material; (2) graft porosity; and (3) thromboresistance. The graft material examined was a fast degrading elastomer, poly (glycerol sebacate) (PGS) because timely degradation allows for rapid host remodeling and mechanical conditioning is recognized as a remodeling cue. An elastomer efficiently transduces mechanical stimulation to the cells. To examine graft porosity, highly porous grafts with interconnected pores to enable immediate host cell infiltration were examined. However, a key requirement of vascular grafts is to prevent bleeding, thus the highly porous graft was enclosed with a leak-proof sheath.

The graft is a foreign material. The inherent response to any blood-contacting foreign material is clotting. Thorough remodeling relies upon cell infiltration into the bulk of the graft, therefore clotting within the graft needed to be controlled as well because extensive blood clotting will reduce cell migration within the graft wall. Thus, the graft was thoroughly coated with heparin, a thromboresistant agent. The resulting open porous graft was suturable and resisted platelet adhesion.

The generated graft included a heparin-coated porous tube wrapped with a 15-µm thin electrospun sheath (FIGS. 1b-1d). The porous tube was made from a rapidly degradable elastomer poly(glycerol sebacate) (PGS) fabricated as previously described in except a 1-mm mandrel was used. The sheath was a 15-µm thin electrospun poly(caprolactone) (PCL) fibrous mesh and served to increase strength. The sheath was porous to accelerate host cells to remodel the graft faster. Thus, the graft relied on controlled fibrin formation within the graft wall to be watertight. The composite grafts were stored dry at ambient temperature in a desiccator until ready to use. Micro-computed tomography (micro-CT) morphometric analysis indicated that the inner diameter of the graft was 720 µm, the wall thickness was 290 µm, and over 99.99% of the pores were interconnected (FIG. 1e). High pore interconnectivity facilitates efficient cell infiltration that is the first step in initiating the host remodeling process. Although the PCL sheath was very thin, it significantly increased the suture retention force of the graft from 0.11±0.0087 to 0.45±0.031 N and was higher than the break force of 9-0 suture (0.26±0.046 N) used for the microsurgical anastomosis (FIG. 1f). Furthermore, the PCL sheath increased elastic tensile modulus from 243±71.8 to 536±119 kPa (p<0.05) and ultimate tensile strength from 76.6±15.7 to 3790±1450 kPa (p<0.001). PGS has numerous OH groups that form hydrogen bonds with heparin. Thus, heparinization of PGS provided a non-thromobogenic lumen of the graft and inhibited excessive blood clotting within the graft wall. In particular, platelet adhesion on the graft reduced significantly upon heparin coating (FIG. 1g) as revealed by lactate dehydrogenase assay. Morphologic examination by scanning electron microscopy (SEM) revealed that heparin coating (2 mg/ml) significantly reduced the number of platelets and fibrin fiber, and most adhered platelets appeared quiescent (FIGS. 1h and 1i). The PCL sheath with very small pore size likely permitted fibrin formation within the sheath to prevent leakage. These studies demonstrated that a disclosed open porous graft was suturable and resisted platelet adhesion.

Example 3

Rapid Cell Infiltration and Graft Remodeling Lead to Strong and Compliant Neo-Artery This example shows rapid cell infiltration and graft remodeling lead to strong and compliant neo-artery.

Interposition grafting of sterilized (ethylene oxide) and heparinized grafts were performed in the abdominal aorta of Lewis rats (n=21) without heparin administration during surgery or systemic heparin treatment after surgery (FIG. 2a). The implantation immediately exposed the grafts directly to 120 mmHg pressure and an arterial hemodynamic environment. Therefore, in terms of allowing unobstructed blood flow immediately upon implantation, the 1-mm synthetic grafts performed the same function as autografts in coronary artery bypass surgeries. The grafts reddened with the infiltration of blood cells, but the PCL sheath effectively prevented bleeding. The host rapidly remodeled patent grafts: by 14 days, the grafts were more translucent and compliant, and began to integrate with the surrounding host tissue; by 90 days, the grafts were covered by a fascia and closely resembled the native aorta and were well integrated with host tissue.

Figure 2B:
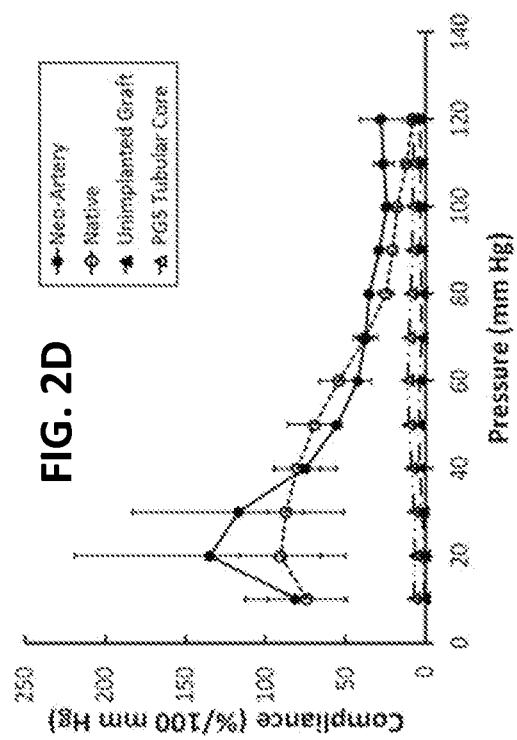
Figure 2C:
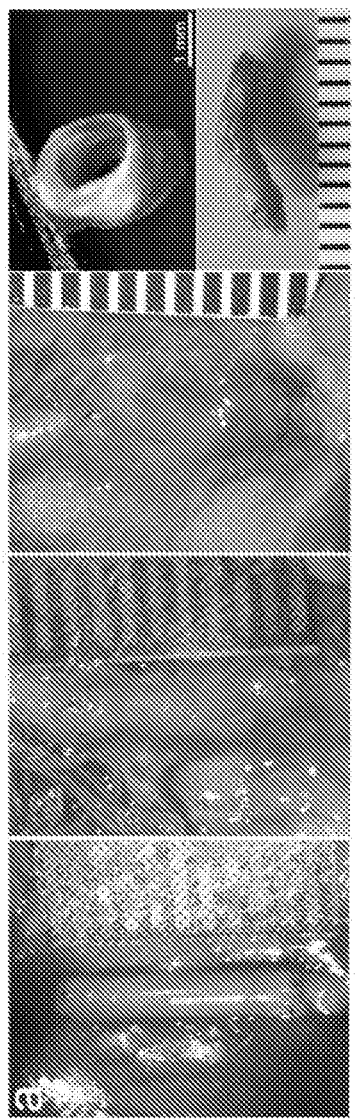
Figure 2D:
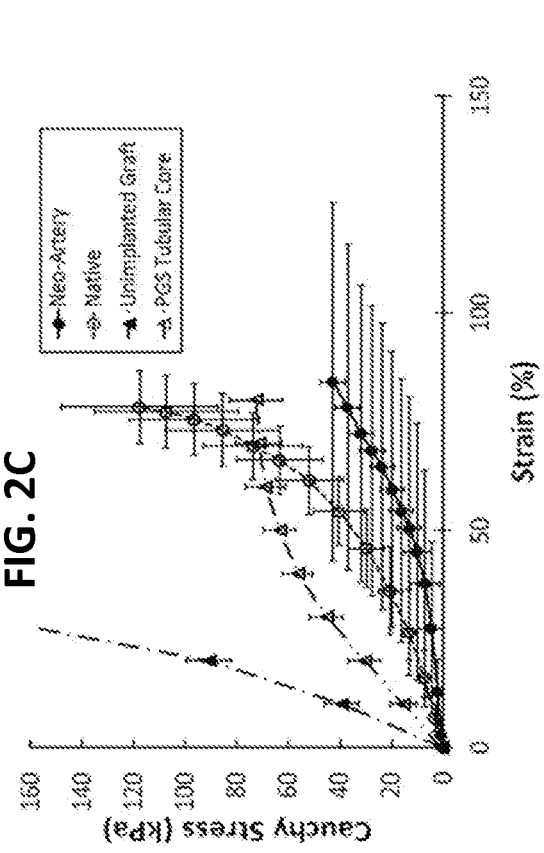

Accompanying the visual remodeling was the pronounced change in mechanical properties. The burst pressure of the neo-arteries was 2360±673 mmHg approaching that of the native aorta at 3415±529 mmHg (FIG. 2b). The burst pressure of the neo-artery is significantly higher than that of human saphenous veins (1680±307 mmHg), the most utilized autografts for coronary artery bypass surgery and lower limb vascular reconstruction. Unimplanted grafts leak due to their high porosity and have no burst pressure to compare. Before implantation, the composite graft was stiffer than the native artery with no toe region in the stress-strain curve (FIG. 2c). Host remodeling substantially altered the stress-strain curve of the graft with a significant toe region appearing after 3 months. The neo-arteries appeared softer than the native aorta, although the differences are insignificant. More importantly, the compliance of the neo-arteries (11±2.2%) was statistically the same as native aorta at 6.7±2.3% in the 80-120 mmHg range. More informative than this highly distilled single value of compliance was a plot of compliance over the whole pressure range (FIG. 2d). Not only was the neo-artery strong, but it was also compliant. The high compliance of neo-arteries contrasted greatly with the lower compliance of unimplanted grafts, suggesting extensive graft remodeling.

This fast host remodeling was explained by widespread cell infiltration soon after implantation. The open porous structure of the graft allowed extensive cell penetration into the graft wall and nucleated cells occupied many of the pores within 3 days (FIG. 7). There was extensive smooth muscle cell infiltration in the graft within 14 days (FIG. 3a). Immuofluorescent staining of α-smooth muscle actin (α-SMA), a protein specific to mural cells including smooth muscle, demonstrated their wide distribution within the graft wall. Higher-magnification images illustrate that smooth muscle cells were not organized into circumferential layers at this early stage, but rather they were mixed α-SMA-negative cells (FIGS. 3b-3c). Co-staining of endothelial and smooth muscle cells indicated that the smooth muscle layer was separated from the blood by an endothelium (FIG. 3d). By 90 days the cellularity of the neo-artery might be slightly higher, but was comparable to that of native aortas (2.14±0.34 vs. 1.36±0.40 µg DNA/mg wet weight, p=0.06). Bright-field images revealed a band of dark spots mixed with cells and generally located closer to the lumen. This acellular matter was likely remnants of graft materials that are visible as dark fibers in bright field images (FIG. 8).

Profound graft remodeling is also reflected at the tissue level in histological observations. Within 14 days the grafts experience extensive degradation (FIGS. 4a-b) and synthesize substantial ECM (FIG. 4b). Therefore, even though the graft material was significantly degraded, the remodeled graft was robust enough to withstand arterial pressure. The luminal area of the graft and the native aorta remained statistically the same throughout the remodeling process, suggesting absence of aneurysm and stenosis (FIG. 4c). The thickness of the graft wall decreased over time but was still thicker than the native aorta at 90 days. The majority of the graft resembled native arteries albeit the ECM fibers were not as dense or as organized. Both the difference in wall thickness and ECM fiber density demonstrates active progressive remodeling of the graft was still active at 3 months.

As expected, macrophages actively participate in the remodeling of the graft: a band of inflammatory cells including newly recruited macrophages (CD68+) was visible beneath the lumen at 14 days. At 28 days, macrophages were distributed more evenly throughout the remodeled grafts at a lower density than 14 days (FIGS. 4d-4f). At 90 days, most of the inflammatory response was resolved with only a small area of the neo-artery positive for macrophages. This trend correlated with the disappearance of the putative graft materials (FIG. 8). Macrophages are heterogeneous with pro-inflammatory (M1) and several alternatively activated (M2) subclasses. Positive staining of CD163 indicates the presence of M2 macrophages that are generally accepted as anti-inflammatory and facilitate constructive remodeling.

Smooth muscle cells are involved in blood vessel functions. Immunofluorescent staining revealed the presence of smooth muscle cells within 14 days and a progressively more organized media layer (FIGS. 4g-4h). The strong expression of myosin heavy chain indicated a contractile phenotype of the smooth muscle cells in the neo-artery (FIG. 4h). Most tissue engineered arteries reported to date typically stain for α-SMA, an early differentiation marker of smooth muscle. On the other hand, myosin heavy chain is a late stage differentiation marker for contractile smooth muscle phenotype. In addition to smooth muscle, neo-arteries also stained positive for fibroblast surface protein in the outer layer at 90 days, indicating the formation of an adventitia-like tissue (FIG. 9). The layers were distinct, resembling the trilaminar structure of a muscular artery.

Figure 5A:
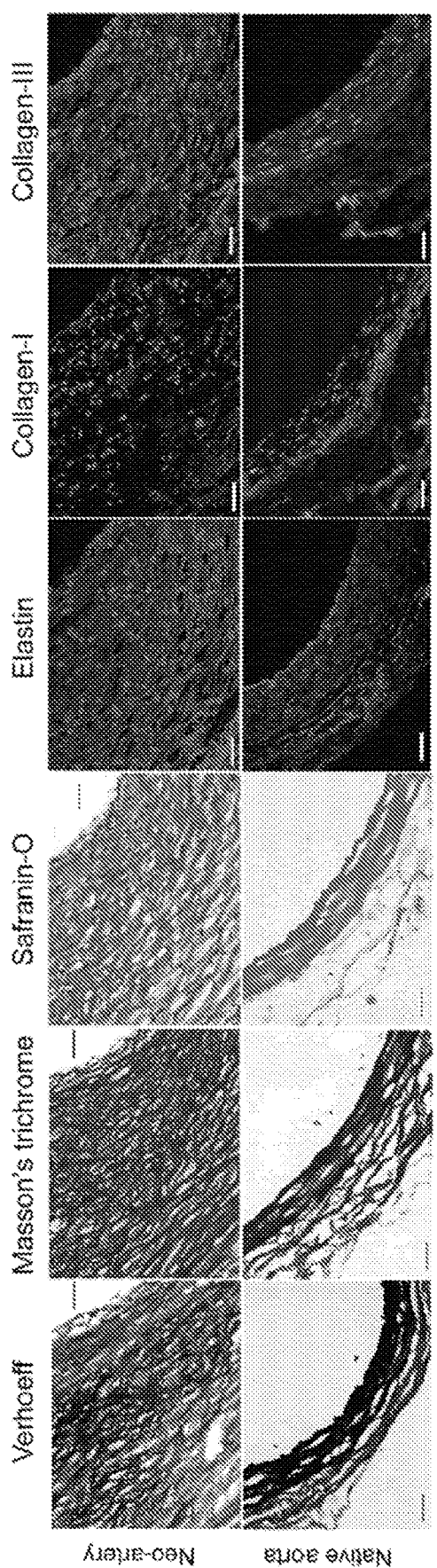
Figure 5B:
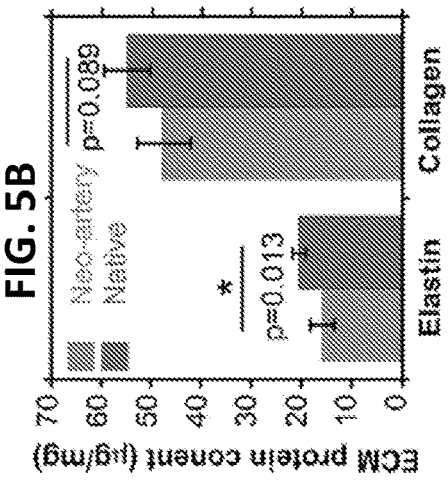

The significant impact of host cells on the graft was further revealed in ECM composition. The neo-artery wall contained significant amounts of elastin, collagen I and III, and glycosaminoglycans (FIG. 5a). The amount of elastin in the neo-artery at 90 days was approximately 77% and total collagen is statistically the same as native aorta (FIG. 5b). All these ECM macromolecules aligned circumferentially, mimicking their orientation in native arteries. However, the native matrix was more compact and less cellular than the neo-artery. Nonetheless, the high ECM production provided a molecular explanation on the observed match of mechanical properties between the neo-artery and the host aorta.

Example 4

Endothelialized Neo-Artery Pulses Synchronously with Host Aorta

This example shows that an endothelialized neo-artery pulses synchronously with a host aorta.

Integration with host tissue is often a significant challenge in tissue engineering. Laser Doppler ultrasound imaging of the disclosed grafts indicated excellent patency and strong and synchronous pulsation with host aorta (FIG. 6a). The regular and clear pulsation of the neo-artery indicated a high-level integration with host tissue. This disclosure is believed to be the first report of any vascular graft that pulses with host arteries. The high patency was corroborated by angiography (FIG. 6b). This correlated well with a confluent endothelial lining revealed by scanning electron microscopy (SEM) of the neo-artery. The transition from host to neo-artery was invisible. The transition was only marked by the presence of the nylon suture (FIG. 6c). The neo-artery was completely endothelialized from the two anastomoses to mid-graft. Von Willebrand factor (vWF) staining revealed a confluent endothelial monolayer covering of the lumen (FIGS. 6d, 6e). Basement membrane separated the endothelial from the smooth muscle layer as indicated by transmission electron microscopy (FIG. 6f). Basement membrane serves the function of preventing smooth muscle cell migration to the endothelial layer, thereby preventing intimal hyperplasia. No evidence of intimal hyperplasia in neo-arteries was observed. In the 4 observed cases of graft occlusion (4/21; 19.0%) the cause was acute anastamotic thrombosis in 3 cases where the animals died. Acute thrombosis was also suspected in one rat that survived with an occluded graft because no graft remodeling was observed in the explant (FIG. 10). Acute thrombosis was likely due to endothelial injury at the anastomosis in the absence of systemic anticoagulation. Overall patency as determined by ultrasonography, angiography and necropsy was 80.9% (17/21) with time points of up to 90 days. Patency rates were 60% (3/5), 100% (5/5), and 81.8% (9/11) for grafts explanted for days 14, 28, and 90, respectively.

Graft material is important to host remodeling. When PCL tubes substituted PGS tubes with all other graft parameters being identical, grafts remodeling was significantly impaired (FIG. 11): Only a thin layer of smooth muscle cells were observed near the lumen. This was consistent with results of other cell-free approaches in arterial tissue engineering where a thin layer of endothelial cells and small amount of smooth muscle were present with graft materials largely intact. The cells within the interstitial space of the graft wall were α-SMA-negative and were potentially inflammatory cells or fibroblasts. The PCL grafts exhibited poor integration with host tissue even at 90 days where a clear boundary was visible and the grafted segment distorted the aorta (FIG. 12). Collagen I expression was much higher than collagen III and elastin. Collagen I distribution was extensive spanning the whole graft area from lumen to albumen (outer surface) whereas other ECM proteins were mostly expressed only near the lumen. Coupling this with the "walled-off" appearance of the H&E stained graft suggests that collagen I might serve to isolate the PCL from the host.

Cell-free approaches to tissue engineering are still provocative and scarce with a focus on slow degrading polymers that lead to prolonged presence of foreign materials. A 1-mm polylactide graft was successfully endothelialized in rats. However, polylactide degraded very slowly causing only partial penetration of smooth muscle cells after 6-month, and no compliance data or ECM content were reported. A similar approach used 10-mm polylactide-polyglycolide composite grafts in canine and porcine models. Large amounts of polymer bundles persisted beyond 12 months, and no elastin content or compliance were reported. Porcine small intestinal submucosa (SIS) grafts demonstrated variable patency above 3 mm diameter, but smaller grafts failed by acute thrombosis despite heparin soaking and systemic heparinization. A 4-mm graft consisting of a porcine small intestinal submucosa collagen layer and cross-linked bovine collagen was populated by endothelial and smooth muscle cells by 3 months in rabbits. However, no mechanical data or ECM content was reported, and the bradykinin vaso-response was counter-physiologic.

Recently a poly(ester urethane)urea elastomeric graft was shown to be populated by endothelial and smooth muscle cells. The grafts contained both collagen and elastin, but the graft material appeared largely intact at 6 months. The cell-free approach has been recently applied in tissue engineering of non-vital organs. A micro-patterned scaffold of polycaprolactone (PCL) and hydroxyapatite-infused with growth factors regenerated the articular surface of rabbit cartilage. Exogenous growth factor was critical for tissue regeneration and resorption of hydroxyapatite is very slow.

The present disclosure differs from the above in that the present emphasizes rapid graft degradation and host remodeling. The utilization of fast degrading synthetic grafts is a new design perspective to vascular substitutes. This disclosure shows nearly complete host remodeling within 3 months post-implantation. The robust yet compliant neo-artery pulses synchronously with the host artery indicate excellent integration.

Many design parameters impact host response. Here, the inventors believe three key features of the reported grafts are fast degradation, elasticity, and pore size. Rapid graft degradation is believed to induce different inflammatory responses as compared to long-lasting materials. Rapid degradation progressively generates more space for cell infiltration, proliferation, and matrix production. Furthermore, fast degradation reduces the duration of host exposure to foreign material. Long-lasting materials cause tissue stiffening from fibrous encapsulation, and can activate inflammatory cells to induce neointimal hyperplasia.

Also matching mechanical properties and optimizing graft pore size contribute to host remodeling and integration. Matching arterial mechanical properties promote vascular cell differentiation and avoid stress shielding. Vascular cells assume more natural phenotypes when cultured on elastomeric substrates. In this current study, the elastic modulus of PGS rather than PCL is believed to dominate in controlling cell phenotype because the majority of graft surface area is PGS. The modulus of PGS is within one order of magnitude of native aortas (148±55 vs. 390±191 kPa) at the strains experienced by new grafts over 80 to 120 mm Hg (FIG. 2c). PGS scaffolds with relatively small pores (20–30 µm) promote smooth muscle elastin production in vitro. Small pores in the disclosed grafts are believed to pack infiltrating cells close together to promote self assembly of cells. The small pores did not seem to inhibit cell infiltration, which may be attributed to both the small diameter of inflammatory cells and the enlargement of pores upon graft degradation.

Although the remodeling process takes over 3 months, a disclosed graft functions like a traditional vascular graft in that it immediately functions as a conduit to allow unobstructed blood flow upon implantation. Thus, this degradable synthetic graft is applicable as coronary and peripheral arterial grafts, and as arteriovenous shunts for dialysis access where "maturation" of 2-3 months is common.

As indicated by the 14-day results, there are significant populations of vWF- and α-SMA-negative cells in the vessel wall. These might be a mixture of progenitor and inflammatory cells. Roh et al. and Hibino et al. recently demonstrated the critical role macrophages play in vascular graft remodeling. A substantial fraction of infiltrating macrophages in the presently disclosed grafts expressed M2 macrophage marker CD163. Recent work by Hibino et al. challenges the view that M2 macrophages suggest regeneration rather than scarring. They found that mouse vena cava grafts with higher M2 activation underwent more stenosis than grafts with less M2. In contrast, none of the disclosed grafts demonstrated stenosis even at 90 days. This may be due to the difference in graft material and design or differences in animal models.

The thickness of the neo-artery wall is not uniform and is thinner where there is residual graft material and inflammation (marked with an *, FIG. 4a). During implantation, the vena cava was separated from the aorta and the fascia covering them was left in place. It is possible that progenitor cells in the adventitia of the cava and the fascia facilitate regeneration via paracrine effects or contribute directly to the regeneration of the neo-artery. It is possible that the part of the grafts that contacts the cava and fascia is remodeled faster, contains more stromal cells and has thicker wall.

A motivation for heparin coating was to increase anti-thrombogenicity. It was possible that heparin coating also promoted graft cellularization and remodeling. Heparin can bind, stabilize, and potentiate the activity of a wide variety of bioactive molecules. Heparin may localize FGF and VEGF families of angiogenic factors to grafts, promoting vascular cell infiltration. Heparin may also promote cellular infiltration by binding cell adhesion proteins such as PECAM-1 and L-selectin, adhesive matrix proteins, and chemokines. Heparinization can improve implant cellularity and angiogenesis. Heparin can also promote remodeling by binding remodeling factors such as tissue plasminogen inhibitor.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A vascular graft, comprising:
   a biodegradable scaffold comprising a biodegradable polyester tubular core of poly(glycerol sebacate) (PGS) having small pores of about 1 µm to about 500 µm and comprising an inner lumen surface and an outer surface; and
   a biodegradable polyester electrospun outer sheath consisting essentially of poly(caprolactone) (PCL) having a thickness between 5 µm and 30 µm and surrounding the outer surface of the biodegradable polyester tubular core, thereby forming a vascular graft; and
   wherein the vascular graft is cell-free.

2. The vascular graft of claim 1, further comprising a thromboresistant agent coating the biodegradable scaffold.

3. The vascular graft of claim 2, wherein the thromboresistant agent comprises heparin.

4. The vascular graft of claim 2, wherein the thromboresistant agent coats the inner lumen surface of the biodegradable polyester tubular core.

5. The vascular graft of claim 1, wherein at least 75% of the pores are interconnected.

6. The vascular graft of claim 1, wherein at least 95% of the pores are interconnected.

7. The vascular graft of claim 1, wherein at least 99% of the pores are interconnected.

8. The vascular graft of claim 1, wherein the vascular graft has an inner diameter of between 700 µm to 5000 µm.

9. The vascular graft of claim 1, wherein the vascular graft has a wall thickness between 100 µm and 500 µm, such as about 290 µm.

10. The vascular graft of claim 1, wherein at least 95% of the vascular graft degrades within 90 days of implantation.

11. The vascular graft of claim 1, wherein the vascular graft is used for forming a blood vessel with a diameter of less than 6 mm.

12. The vascular graft of claim 1, wherein the vascular graft is used as a coronary or a peripheral arterial graft.

13. The vascular graft of claim 1, wherein the biodegradable scaffold comprises a wall thickness of from 100 μM to 500 μM.

14. The vascular graft of claim 1, wherein at least 90% of the vascular graft degrades within 12 weeks of implantation in a subject.

15. The vascular graft of claim 1, wherein the vascular graft is used for forming a blood vessel with a diameter of less than 4 mm.

* * * * *